(12) United States Patent
Strauch et al.

(10) Patent No.: US 11,185,381 B2
(45) Date of Patent: *Nov. 30, 2021

(54) SURGICAL DRAPE WITH SEPARABLE ELEMENTS

(71) Applicant: Creative Surgical Solutions, LLC, Vail, CO (US)

(72) Inventors: Eric Strauch, Vail, CO (US); Donald Corenman, Edwards, CO (US); Dan Droy, Denver, CO (US)

(73) Assignee: Creative Surgical Solutions, LLC, Vail, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/435,495

(22) Filed: Jun. 8, 2019

(65) Prior Publication Data

US 2019/0290377 A1    Sep. 26, 2019

Related U.S. Application Data

(63) Continuation of application No. 14/846,388, filed on Sep. 4, 2015, now Pat. No. 10,363,108, which is a
(Continued)

(51) Int. Cl.
*A61B 46/00* (2016.01)
*A61B 17/00* (2006.01)

(52) U.S. Cl.
CPC .... *A61B 46/00* (2016.02); *A61B 2017/00902* (2013.01)

(58) Field of Classification Search
CPC ......... A61B 46/00; A61B 46/20; A61B 46/27; A61B 46/30; A61B 2046/205; A61B 46/40; A61B 2090/037; A61B 2017/00902

See application file for complete search history.

(56) References Cited

U.S. PATENT DOCUMENTS 2,353,858 A    7/1944    Tedesco
RE24,613 E    3/1959    Hageltorn
(Continued)

FOREIGN PATENT DOCUMENTS

CN    1214625    4/1999
CN    101721255    6/2020
(Continued)

OTHER PUBLICATIONS

File History of U.S. Appl. No. 61/352,045, filed Jun. 7, 2010.
(Continued)

*Primary Examiner* — Camtu T Nguyen
(74) *Attorney, Agent, or Firm* — Sheridan Ross P.C.

(57) ABSTRACT

The present disclosure relates to a surgical drape to be used in conjunction with a surgical procedure, and more specifically to a surgical drape that includes one or more of the following: (1) a patient drape for use with a standalone non-draped image acquisition device; (2) a patient drape for use with a standalone non-draped image acquisition device with image guidance navigation technology; (3) the means to provide temporary sterile coverage of an underlying sterile field; (4) the means to provide sterile separation of at least a portion, if not the entire temporary sterile coverage; and (5) the means to provide covering of the undersurface of the operating surface and enclosing any suspended medical devices, wires, cables, tubes, etc.

7 Claims, 35 Drawing Sheets

Related U.S. Application Data continuation-in-part of application No. 14/280,416, filed on May 16, 2014, now Pat. No. 10,363,110, which is a continuation of application No. 13/155,219, filed on Jun. 7, 2011, now Pat. No. 8,726,907, said application No. 16/435,495 is a continuation-in-part of application No. 14/280,416, filed on May 16, 2014, now Pat. No. 10,363,110.

(60) Provisional application No. 62/046,029, filed on Sep. 4, 2014, provisional application No. 61/352,045, filed on Jun. 7, 2010, provisional application No. 61/357,637, filed on Jun. 23, 2010, provisional application No. 61/490,432, filed on May 26, 2011.

(56) References Cited

U.S. PATENT DOCUMENTS

| | | | |
|---|---|---|---|
| 2,960,561 | A | 11/1960 | Plummer |
| 3,060,932 | A | 10/1962 | Pereny et al. |
| 3,255,809 | A | 6/1966 | Kawczynski |
| 3,682,163 | A | 8/1972 | Plummer |
| 3,698,395 | A | 10/1972 | Hansson |
| 3,741,203 | A | 6/1973 | Liman |
| 3,835,851 | A | 9/1974 | Villari |
| 3,882,859 | A | 5/1975 | Ericson |
| 4,090,508 | A | 5/1978 | Gaylord, Jr. |
| 4,153,054 | A | 5/1979 | Boone |
| 4,369,356 | A | 1/1983 | Tsurutani et al. |
| 4,627,426 | A | 12/1986 | Wegener et al. |
| 4,782,502 | A | 11/1988 | Schulz |
| 4,873,997 | A | 10/1989 | Marshall |
| 4,887,339 | A | 12/1989 | Bellanger |
| 4,905,710 | A * | 3/1990 | Jones ................ A61F 13/00 128/849 |
| 4,939,819 | A | 7/1990 | Moyer |
| 5,127,423 | A | 7/1992 | Draeger |
| 5,187,813 | A | 2/1993 | Klein |
| 5,263,970 | A | 11/1993 | Preller |
| 5,503,163 | A | 4/1996 | Boyd |
| 5,515,868 | A | 5/1996 | Mills |
| 5,527,312 | A | 6/1996 | Ray |
| 5,569,246 | A | 10/1996 | Ojima et al. |
| 5,605,534 | A | 2/1997 | Hutchison |
| 5,651,375 | A | 7/1997 | Cunningham |
| 5,674,189 | A | 10/1997 | McDowell et al. |
| 5,810,750 | A | 9/1998 | Buser |
| 5,817,038 | A | 10/1998 | Orange et al. |
| 5,865,846 | A | 2/1999 | Bryan et al. |
| 6,030,401 | A | 2/2000 | Marino |
| 6,113,602 | A | 9/2000 | Sand |
| 6,142,998 | A | 11/2000 | Smith et al. |
| 6,286,511 | B1 | 9/2001 | Levitt et al. |
| 6,290,724 | B1 | 9/2001 | Marino |
| 6,309,395 | B1 | 10/2001 | Smith et al. |
| 6,314,959 | B1 | 11/2001 | Griesbach et al. |
| 6,328,738 | B1 | 12/2001 | Suddaby |
| 6,364,880 | B1 | 4/2002 | Michelson |
| 6,719,795 | B1 | 4/2004 | Cornwall et al. |
| 7,014,640 | B2 | 3/2006 | Kemppanien et al. |
| 7,025,769 | B1 | 4/2006 | Ferree |
| 7,077,864 | B2 | 7/2006 | Byrd, III et al. |
| 7,182,088 | B2 | 2/2007 | Jenkins |
| 7,207,992 | B2 | 4/2007 | Ritland |
| 7,288,093 | B2 | 10/2007 | Michelson |
| 7,341,590 | B2 | 3/2008 | Ferree |
| 7,387,643 | B2 | 6/2008 | Michelson |
| 7,406,775 | B2 | 8/2008 | Funk et al. |
| 8,726,907 | B2 | 5/2014 | Strauch et al. |
| 1,036,310 | A1 | 7/2019 | Corenman et al. |
| 1,036,311 | A1 | 7/2019 | Strauch et al. |
| 1,061,032 | A1 | 4/2020 | Ueda |
| 2006/0064797 | A1 | 3/2006 | Rowe et al. |
| 2006/0137693 | A1 * | 6/2006 | Lewis ................ A61B 19/00 128/853 |
| 2007/0162096 | A1 | 7/2007 | Zakuto et al. |
| 2008/0000006 | A1 | 1/2008 | Ochoa et al. |
| 2008/0168995 | A1 | 7/2008 | Yarclan et al. |
| 2008/0255564 | A1 | 10/2008 | Michelson |
| 2009/0277460 | A1 | 11/2009 | Carrez et al. |
| 2010/0031966 | A1 | 2/2010 | Allen |
| 2010/0186754 | A1 * | 7/2010 | Carrez ................ A61B 19/08 128/853 |
| 2010/0192960 | A1 | 8/2010 | Rotolo |
| 2013/0072839 | A1 | 3/2013 | Cuypers et al. |
| 2014/0081291 | A1 | 3/2014 | Groke et al. |
| 2015/0114404 | A1 | 4/2015 | Czop et al. |
| 2019/0060020 | A1 | 2/2019 | Toure |

FOREIGN PATENT DOCUMENTS

| | | |
|---|---|---|
| FR | 2896146 | 7/2007 |
| WO | WO 2017/040454 | 3/2017 |

OTHER PUBLICATIONS

File History of U.S. Appl. No. 61/357,637, filed Jun. 23, 2010.
International Search Report for International Patent Application No. PCT/US2012/039555, dated Sep. 14, 2012, 3 pages.
Written Opinion for International Patent Application No. PCT/US2012/039555, dated Sep. 14, 2012, 4 pages.
International Preliminary Report on Patentability for International (PCT) Patent Application No. PCT/US2012/039555, dated Apr. 10, 2014 6 pages.
Official Action (with English Translation) for China Patent Application No. 2012800255508, dated Nov. 30, 2015 19 pages.
Notice of Allowance (with English translation) for China Patent Application No. 201280025550.8, dated Nov. 18, 2016 9, 5 pages.
Extended Search Report for European Patent Application No. 12789811.2, dated May 11, 2015 6 pages.
Article 94(3) Communication for European Patent Application No. 12789811.2, dated Oct. 8, 2019, 6 pages.
Official Action (no English translation available) for Mexican Patent Application No. MX/a/2019/011486, dated Jul. 23, 2020, 3 pages.
International Search Report and Written Opinion for International (PCT) Patent Application No. PCT/US16/49358, dated Nov. 10, 2016, 8 pages.
International Preliminary Report on Patentability for International (PCT) Patent Application No. PCT/US2016/049358, dated Mar, 15, 2018, 7 pages.
Extended European Search Report for European Patent Application No. 18191933.3, dated Jan. 17, 2019, 8 pages.
Official Action for U.S. Appl. No. 13/155,219 dated Nov. 21, 2012, 9 pages.
Official Action for U.S. Appl. No. 13/155,219, dated May 17, 2013 9 pages.
Official Action for U.S. Appl. No. 13/155,219, dated Sep, 13, 2013 12 pages.
Notice of Allowance for U.S. Appl. No. 13/155,219, dated Mar. 28, 2014 9 pages.
Official Action for U.S. Appl. No. 14/280,416, dated Oct. 26, 2016, 20 pages.
Official Action for U.S. Appl. No. 14/280,416, dated Mar. 14, 2017, 20 pages.
Official Action for U.S. Appl. No. 14/280,416, dated Jul. 12, 2017, 16 pages.
Official Action for U.S. Appl. No. 14/280,416, dated Mar. 22, 2018, 17 pages.
Official Action for U.S. Appl. No. 14/280,416, dated Dec. 13, 2018, 18 pages.
Notice of Allowance for U.S. Appl. No. 14/280,416, dated Mar. 6, 2019, 10 pages.
Official Action for U.S. Appl. No. 14/846,388, dated Oct. 4, 2016, 20 pages.
Official Action for U.S. Appl. No. 14/846,388 dated Feb. 8, 2018, 14 pages.
Official Action for U.S. Appl. No. 14/846,388 dated Mar. 30, 2018, 15 pages.

(56) References Cited

OTHER PUBLICATIONS

Official Action for U.S. Appl. No. 14/846,388 dated Sep. 24, 2018, 16 pages.
Notice of Allowance for U.S. Appl. No. 14/846,388 dated Mar. 15, 2019, 9 pages.
Official Action for U.S. Appl. No. 16/119,205, dated Dec. 2, 2020, 11 pages.

* cited by examiner

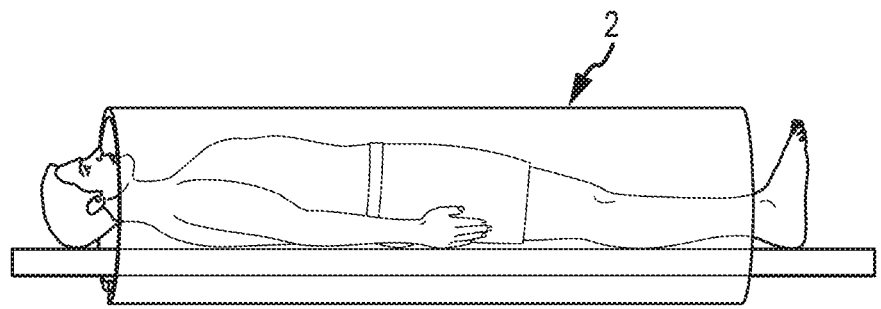
FIG.1A
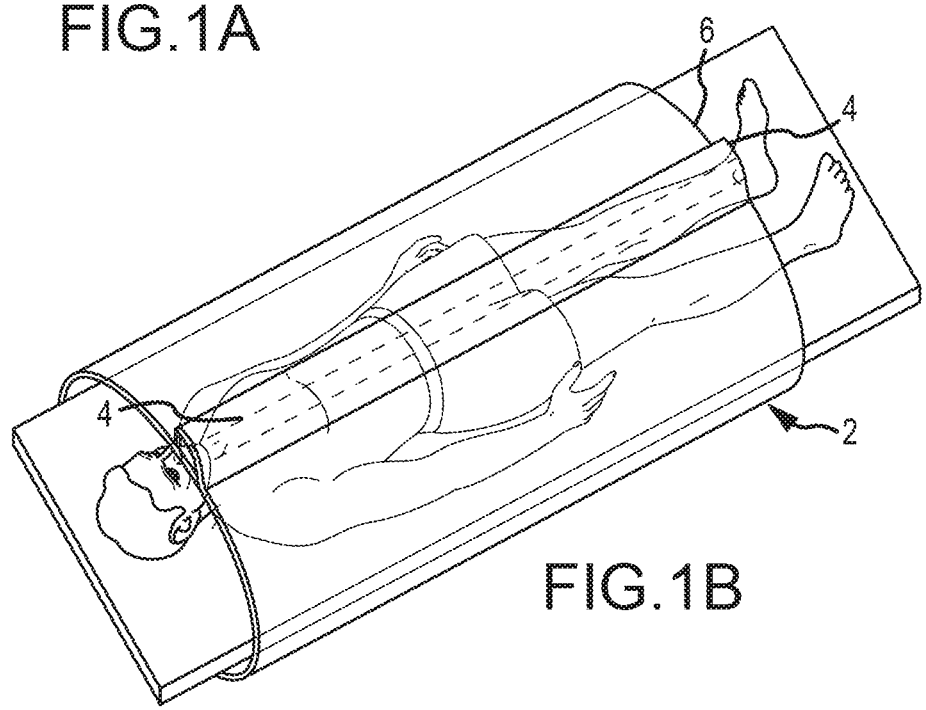
FIG.1B
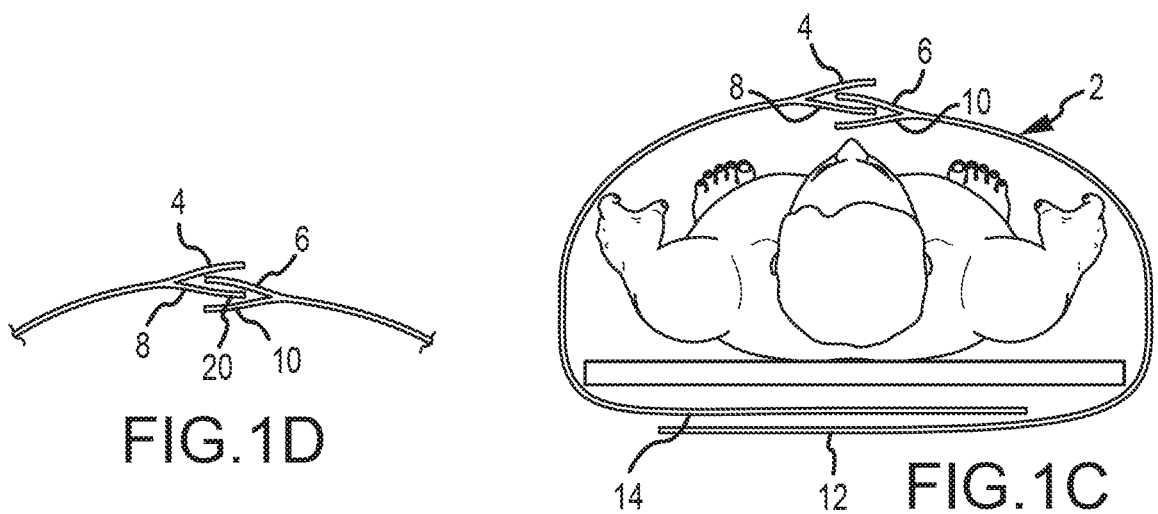
FIG.1D
FIG.1C

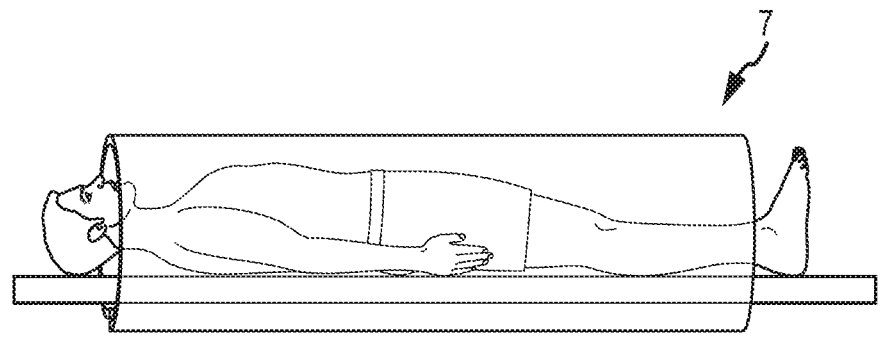
FIG.6A
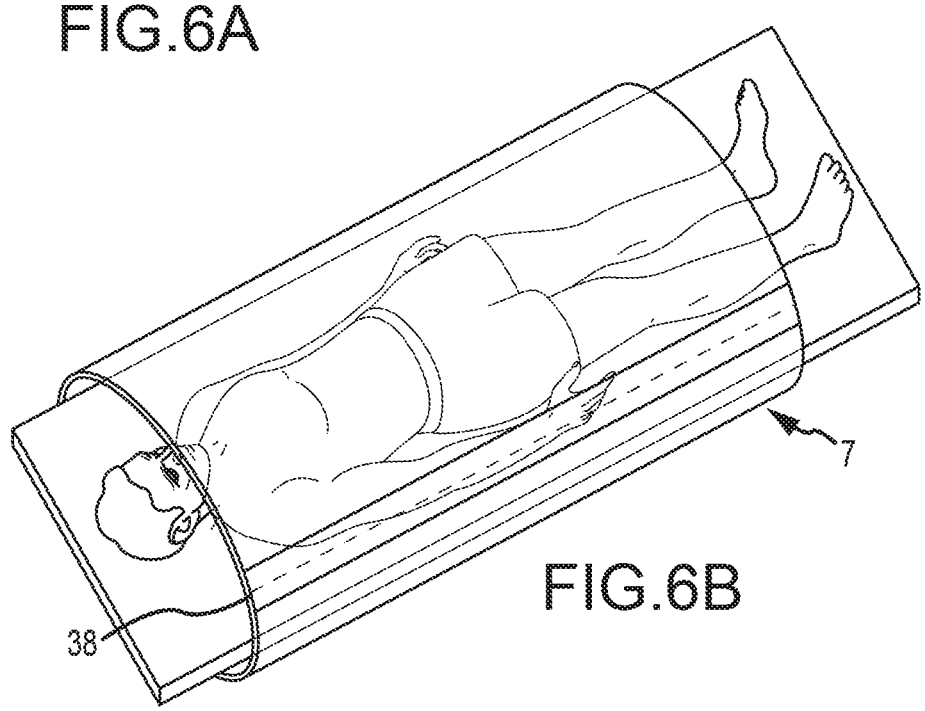
FIG.6B
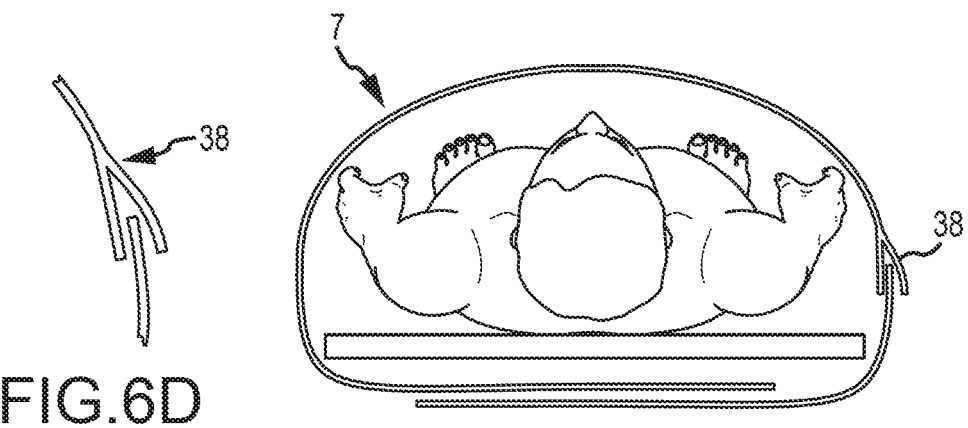
FIG.6D
FIG.6C

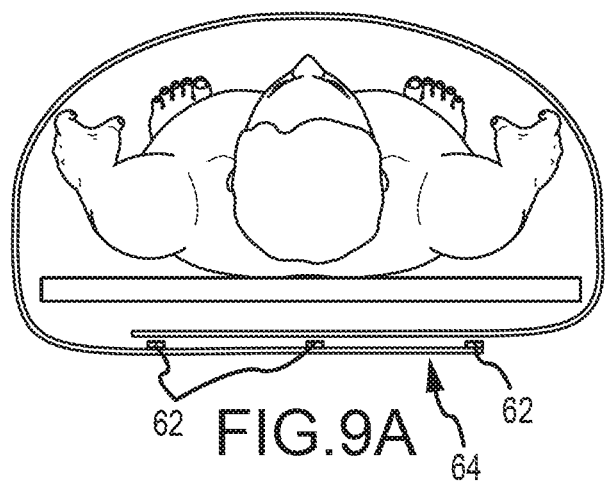
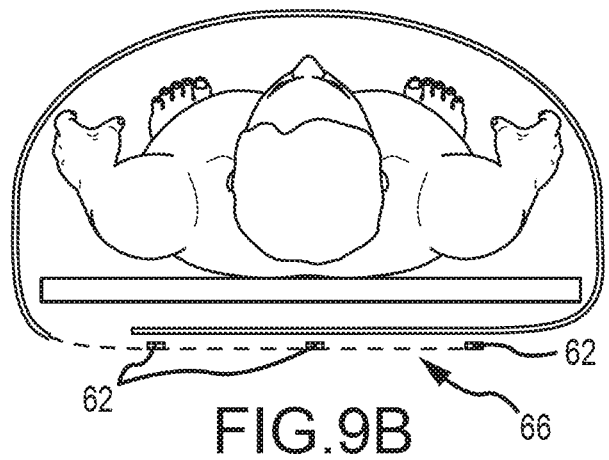
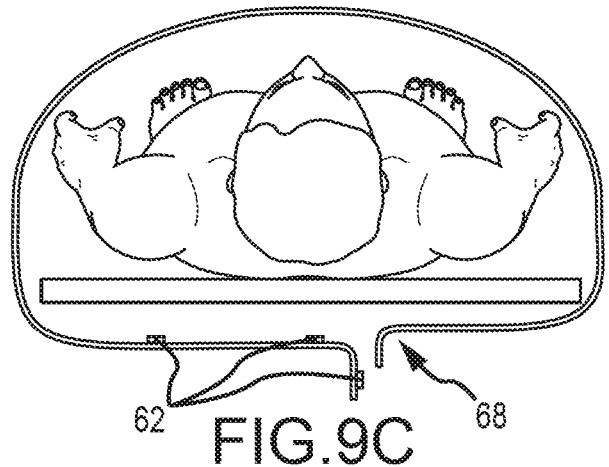

FIG. 15A
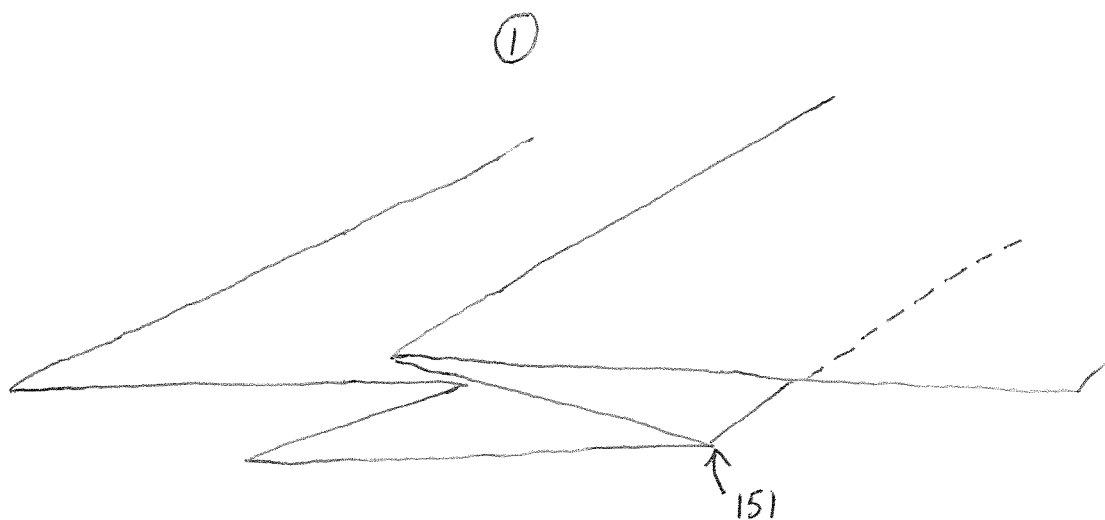
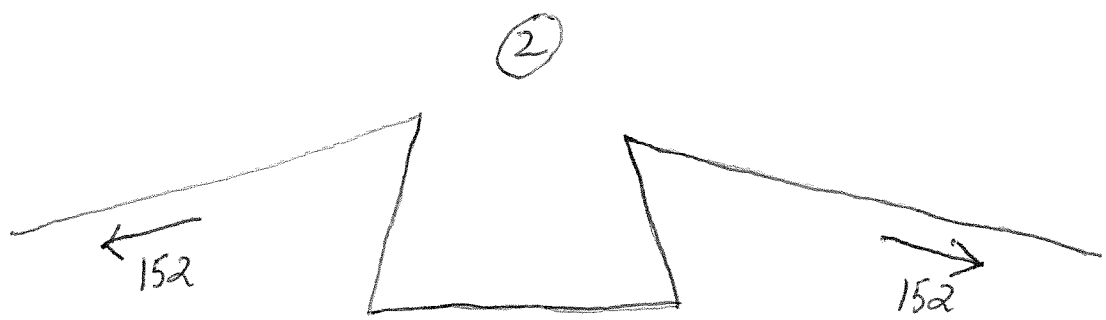
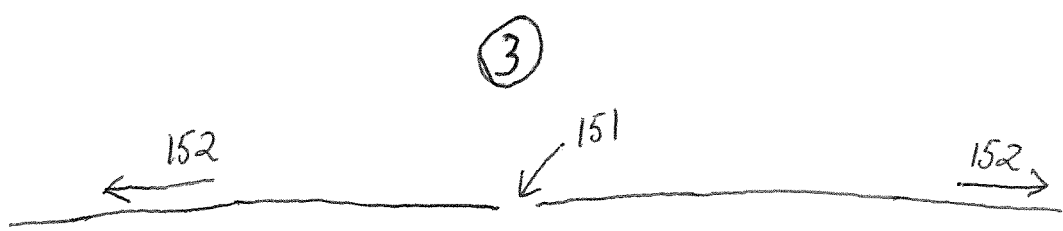

FIG. 15C
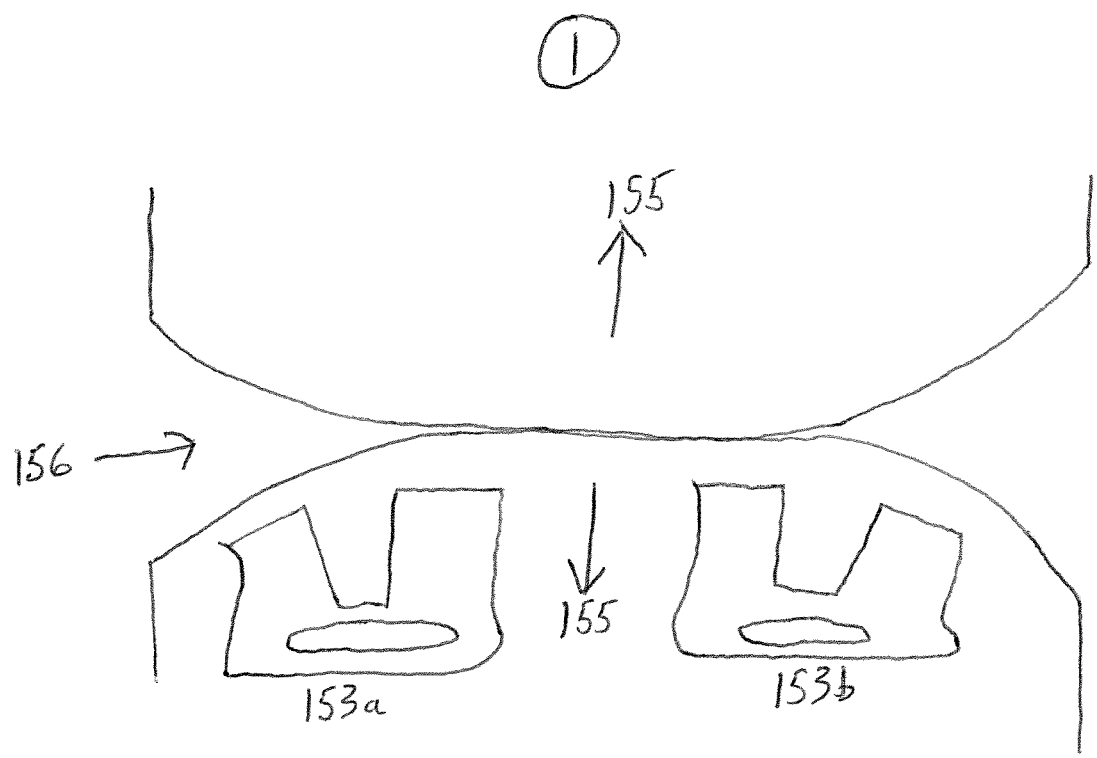
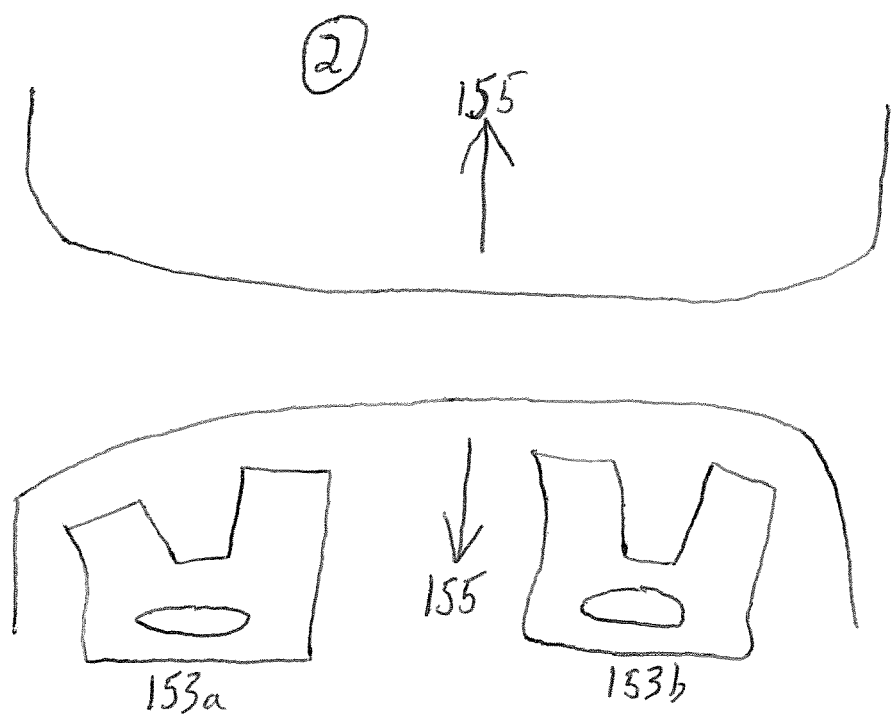

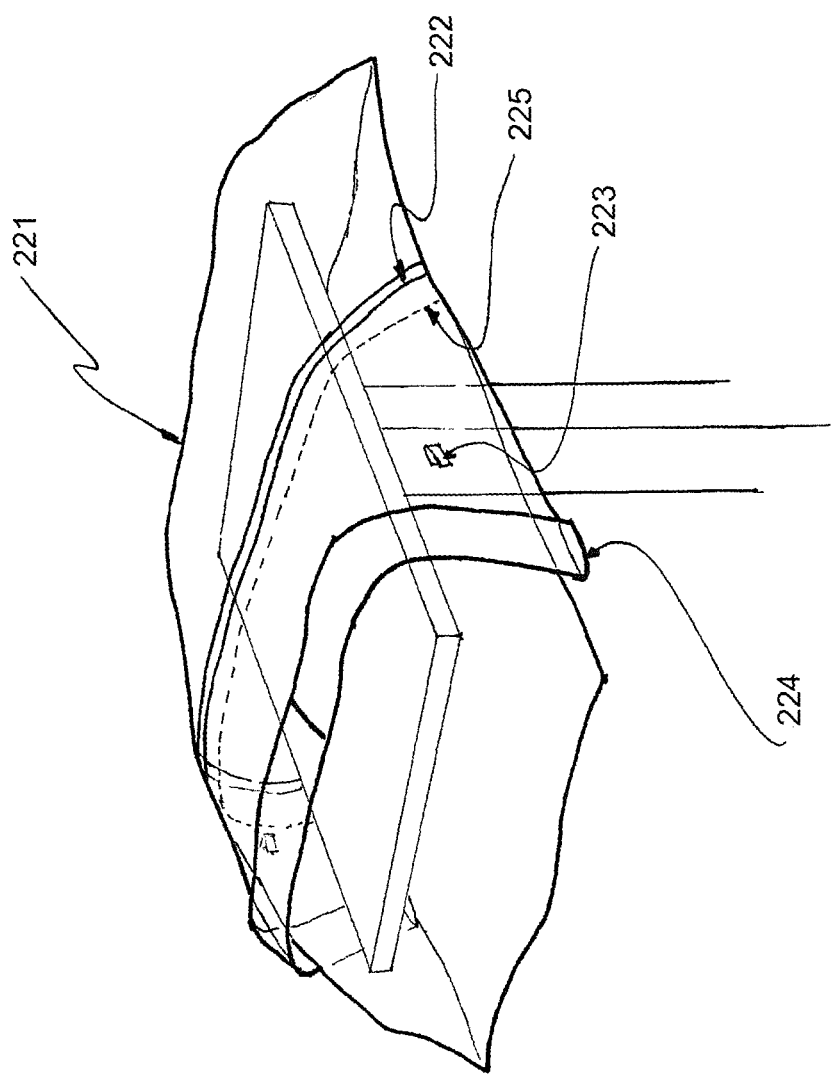

SURGICAL DRAPE WITH SEPARABLE ELEMENTS

CROSS-REFERENCE TO RELATED APPLICATIONS

The present application is a continuation of U.S. patent application Ser. No. 14/846,388, filed Sep. 4, 2015, which claims priority from U.S. Provisional Application No. 62/046,029, filed Sep. 4, 2014, and is also a continuation-in-part of U.S. patent application Ser. No. 14/280,416, filed May 16, 2014, which in turn is a continuation of U.S. patent application Ser. No. 13/155,219, filed Jun. 7, 2011, now patented as U.S. Pat. No. 8,726,907, which in turn claims priority from U.S. Provisional Application Nos. 61/352,045, filed Jun. 7, 2010, 61/357,637 filed Jun. 23, 2010, and 61/490,432 filed May 26, 2011. The present application is also a continuation-in-part of U.S. patent application Ser. No. 14/280,416, filed May 16, 2014. The disclosures of all of the above-referenced applications are hereby incorporated by reference in their entireties.

FIELD OF THE INVENTION

This disclosure relates to orthopedic surgery, and more specifically to a surgical drape that includes one or more of the following: (1) a patient drape for use with a standalone non-draped image acquisition device (requiring circumferential access to the patient); (2) a patient drape for use with a standalone non-draped image acquisition device with image guidance navigation technology; (3) the means to provide temporary sterile coverage of an underlying sterile field; (4) the means to provide sterile separation of at least a portion, if not the entire temporary sterile coverage; and (5) the means to provide covering of the undersurface of the operating surface and enclosing any suspended medical devices, wires, cables, tubes, etc.

BACKGROUND OF THE INVENTION

Individuals may suffer a variety of spinal disorders involving degenerative disc disease, spine deformity, herniated discs, traumatic injuries and congenital anomalies. Some of these pathologies may require surgery on the affected region to relieve the individual from pain and/or prevent further injury to the spine and neural structures. Spinal surgery may involve decompression of the spinal cord and nerves, stabilization of painful or unstable motion segments and correction of deformity. The surgical procedure will vary depending on the nature and extent of the pathology. In all instances, it is critical that a sterile field be maintained throughout the procedure, regardless of its duration. Published standards and recommended practices exist, including those developed by the Association of periOperative Registered Nurses (AORN), which provide guidelines to be used by a surgical team when caring for their patients in an operative setting.

It is the goal of the surgical team to prevent the contamination of an open surgical wound by isolating the operative site from the surrounding nonsterile environment. The surgical team accomplishes this by creating and maintaining the sterile field and by following aseptic principles aimed at preventing microorganisms from contaminating the surgical wound. Sterile surgical drapes establish an aseptic barrier minimizing the passage of microorganisms from nonsterile to sterile areas. Sterile drapes should be placed on the patient, furniture, and equipment to be included in the sterile field, leaving only the incisional site exposed. During the draping process, only scrubbed personnel should handle sterile drapes. The drapes should be held higher than the operating room bed with the patient draped from the prepped incisional site out to the periphery. According to the standards published by AORN, once the sterile drape is positioned, it should not be moved or rearranged.

Several disadvantages exist regarding current methods for maintaining sterility throughout a spinal surgery. First, current makeshift draping procedures (fitting a multitude of drapes around the patient) are time consuming and thus prolong the length of the procedure. Second, current methods of draping the various equipment and surgical implements are complicated and challenging to accomplish efficiently. Third, maintaining a sterile field throughout the procedure is more challenging, especially when using radiological equipment. Finally, current draping systems do not provide a well-accepted means to provide temporary sterile coverage of underlying sterile equipment tables and trays.

Currently, navigation technology in conjunction with three dimensional ("3D") radiographic technology is being utilized to make surgical techniques more time-efficient, accurate, and safer. Using 3D imaging by utilizing an "O-arm" device (with or without navigation technology) presents challenges both in regard to appropriate draping and maintenance of a sterile field as well as maneuverability of the 3D imaging device in and out of the sterile field. "C-arm" surgical cases can present similar challenges.

In regards to the above-referenced radiological equipment, to create a sterile "tunnel" with drapes through which the arm can pass (as it rises from the unsterile 'below table' region to the sterile 'above table region') is not only cumbersome and time-consuming, but also a potential risk to the sterile field if such a method were to fail (e.g., an unsterile drape falls into the sterile field as the radiological device arm propels it superiorly).

Sleeve type drapes for covering an 'O-arm' have been utilized. Aside from the fact that they are time-intensive and cumbersome, these drapes can contaminate the field if they become displaced as the O-arm is enclosing around the OR table. Also, the sag of the drape off the underside of the most superior aspect of the O-arm can block the reference frame from being properly read and displayed by the monitor. Finally, given the effort necessary in draping the 3D radiological device itself, the surgeon may decide to leave the device in the field and operate around it, thereby avoiding having to re-drape again for later imaging. Thus, the surgeon is compromised as he/she attempts to perform the surgery with the 3D device left in place.

Currently, many surgeons utilizing a 3D acquisition device in conjunction with navigation technology have devised makeshift draping systems that, while draping the patient rather than the radiographic device for reasons stated above, attempt to maintain complete protection to the underlying sterile field. The reference frame attached to the patient's anatomy (often the spinous process) must protrude through the disposable, makeshift draping system (formed by two approximated half sheets secured by steri-strips) in order to be readable by the navigation monitor. However, the reference frame cannot be exposed to the underside of the undraped (and thus non-sterile) 3D radiographic device above. Therefore, the reference frame is often covered by a piece of clear plastic to maintain the sterility of the reference frame attached to the patient's anatomy, but at the same time, allow for the reference frame to be readable by the navigation monitor. This piece of clear plastic also serves another purpose—it covers the medial borders of both approximated half-sheets that run longitudinally along the sagittal midline of the patient through which the reference frame neck protrudes. When removing this makeshift draping system, the plastic cover is removed, followed by the fall of both half sheets laterally off the table.

Numerous problems exist in regard to draping when attempting to use 3D devices and concomitantly maintain a sterile field. In regard to the makeshift draping system described above, several concerns are raised. First, any breach in the makeshift drape system (e.g. gap, tear or opening) can potentially cause the drape to fail in its intended purpose—protecting the patient from infection by preventing microorganisms from making their way into the skin opening of the surgical site. For instance, the plastic covering of the reference frame and medial borders of the two approximated half sheets often does not extend the entire length of the half-sheets. Thus, if the 3D radiographic device swings into position over any portion of the approximated half-sheets uncovered by the plastic cover, the medial borders are potentially exposed. When the half-sheets fall laterally to the floor during the removal process, it is possible that contamination of the underlying sterile field could occur as the medial edges of the half-sheets make contact. Second, the time in gathering the components of such a makeshift draping system (2 half-sheets, two non-piercing hemostats/clamps, steri-strips, and a cut out plastic covering) and placing into position is labor and time-intensive. Certainly, it can be expected that any relatively new scrub technician will not have such components ready in an efficient manner.

The accuracy of integration of the anatomical information provided by the 3D data acquisition device and the navigation system depends on the technology utilized, the readability of the reference frame, and the stability of the reference frame. Under the assumption that medical providers are content with the technological capabilities of the system, the two remaining variables regarding accuracy of integration of anatomical data and monitored (navigated) surgical instruments are the readability and stability of the reference frame. Under the assumption that medical providers remain meticulous in avoidance of reference frame displacement, then the remaining factor affecting the accuracy of the system is based on the readability of the reference frame. A thin, clear plastic is therefore desirable to minimize refraction of the infrared light thereby minimizing any inaccuracy that may inherently exist with indirect communication of the navigation monitor and the reference frame.

Thus, multiple problems exist in prior art draping apparatus and methods, and in particular providing a sterile field where a separation is necessary to accommodate one or more pieces of equipment used during the surgery. Because the use of makeshift draping is both time and labor intensive, does not adequately address the helpful 'under the table' enclosure, and fails to preserve sterile technique, many surgeons have opted to simply not drape the sterile fields as well as the 3D radiographic device. The present disclosure addresses all of these challenges and other shortcomings in the prior art.

SUMMARY OF THE INVENTION

This disclosure relates to orthopedic surgery, and more specifically to a one piece customized disposable surgical drape that includes one or more of the following: (1) a patient drape for use with a standalone non-draped image acquisition device (requiring circumferential access to the patient); (2) a patient drape for use with a standalone non-draped image acquisition device with image guidance navigation technology; (3) the means to provide temporary sterile coverage of an underlying sterile field; (4) the means to provide sterile separation of at least a portion, if not the entire temporary sterile coverage; and (5) the means to provide covering of the undersurface of the operating surface and enclosing any suspended medical devices, wires, cables, tubes, etc.

According to one embodiment, an apparatus is disclosed wherein a draping device is utilized for concomitant use of navigation technology and 3D imaging, featuring 'through plastic (or lens) readability, sterile longitudinal separation, and under-table wrapping capability, as described in greater detail below.

According to one embodiment, an apparatus is disclosed wherein a draping device further allows for navigation readability of one or more reference frames both indirectly (through plastic or lens) and directly (without plastic or lens). The level of sterility depends on the option chosen. Sterile longitudinal separation of the draping device in one or more locations and under-table wrapping capabilities are similarly provided with this embodiment.

According to one embodiment, an apparatus is disclosed wherein a draping device is provided to offer temporary coverage for an underlying sterile field (without navigation technology). This may involve 2D or 3D imaging without navigation (e.g. no reference frame) or temporary sterile coverage of a sterile or equipment table. The drape of this embodiment has a longitudinal sterile separation element, and the under-table wrapping capability may also be provided. The plastic component may be provided, or alternatively the draping device may be manufactured as a plastic or transparent paper drape, or similar transparent material.

Navigation and 3D Imaging Use

When performing a 3D imaging or a radiological procedure, the equipment and imaging technology often requires that a patient has a sterile reference frame attached to and protruding from his/her anatomy that needs to be readable by a navigation monitor while 3D imaging is obtained. The surgical drape device according to one embodiment is designed to drape the sterile field rather than the radiological device. It accommodates a surgeon's preference, as it allows for navigation readability of the attached reference frame through a clear plastic material or optical lens while the 3D acquisition is taking place.

Incorporation of a clear plastic region or lens into the drape device preserves sterility of the underlying reference frame and surgical field, while simultaneously allowing for readability of the reference frame by the navigation device. In spine surgery, the surgical drape permits reference frame placement in the posterior cervical, thoracic and lumbar spine axial positions, as well as the posterior superior iliac crest position (on either side). The drape device therefore accommodates different anatomical placements of the reference frame (such as when utilized in maxillofacial/ENT surgery and pelvic trauma) and/or various positions of the monitor, such as for cranial positioning.

Sterile Separation of Two Opposing Edges

The draping device according to varying embodiments provides at least one location for achieving a longitudinal separation of the drape, while still maintaining the sterility of the separating edges, and allows for easy removal of the drape. The two separating halves of the drape can fall to their respective side of the OR table in a sterile manner, thus exposing the underlying sterile field for continuance of surgery. Several unique arrangements and mechanisms for sterile separation are described below.

This particular embodiment is critical where a surgical patient is draped, rather than a radiological device. However, the sterile separation of two opposing edges may also be applied to a drape utilized in a variety of non-radiographic imaging situations where temporary coverage of a sterile field is necessary. Examples of such uses are also described below.

Under-Table Wrap Up Component

According to another embodiment, the drape device allows for complete enclosure of the patient not only above the table but also underneath the table (in the unsterile region). The portion of the drape underneath the table will clasp in one or more locations to enclose the various wires, cords, and tubes (e.g. neuromonitoring wires, catheter, etc.) and allow for easy and efficient positioning (entrance and exit) of any required non-sterile 2D or 3D image data acquisition device around the table and patient.

When 2D or 3D imaging is used as a standalone device (and thus without concomitant use of navigation technology), the drape still offers desirable improvements over the prior art in the sterile separation of two longitudinal opposing edges (e.g. 'double underbite' separation) as well as the 'under-the-table' wrapping component, both making surgery safer and more efficient.

In one embodiment, a drape is provided with a selectively separable portion intersecting a lateral point proximal to a midpoint of a predetermined width of the drape. In a further embodiment, a drape comprises a selectively separable portion intersecting a lateral point that is proximal to a midpoint of a predetermined width of the drape and within a middle third of the predetermined width. In a further embodiment, a drape comprises a selectively separable portion intersecting a lateral point that is proximal to a midpoint of a predetermined width of the drape and wherein the midpoint is equidistant from the first peripheral edge and the second peripheral edge of the drape.

Surgical Back Table Use

According to one embodiment, the drape allows for the maintenance of sterility of a table where surgical instruments are kept while not in use, commonly referred to as a "back table," and the instruments and equipment thereon. The two halves of the drape may be separated and drawn away from the back table on opposing sides, such that no dust, debris or foreign items fall from the drape onto the back table and thus contaminate it. After the two halves of the drape have been separated and the drape has been removed, the instruments and equipment on the operating table may be accessed by a surgeon or his or her assistants when needed to continue the surgery.

Mayo Stand Cover

According to one embodiment, the drape allows for the maintenance of sterility of a movable or repositionable instrument stand, commonly referred to as a "Mayo stand," and the instruments and equipment thereon. The drape may have multiple separable sections, which may be pulled apart along a perforation or other separating line and drawn away from or off of the mayo stand, such that no dust, debris, or foreign items fall from the drape onto the stand and thus contaminate it. After the drape has been removed, the instruments on the mayo stand may be accessed by a surgeon or his or her assistants when needed to continue the surgery.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 1A is a side elevation view of a patient with a draping device according to one embodiment of the present disclosure;

FIG. 1B is a top perspective view of the draping device shown in FIG. 1A;

FIG. 1C is an end view of the draping device shown in FIG. 1A;

FIG. 1D is a partial sectional view of the draping device shown in FIG. 1A;

FIG. 6A is a side elevation view of a patient with a draping device according to one embodiment of the present disclosure;

FIG. 6B is a top perspective view of the draping device shown in FIG. 6A;

FIG. 6C is an end view of the draping device shown in FIG. 6A;

FIG. 6D is a detailed sectional view of the draping device shown in FIG. 6A;

FIG. 9A is an end view of a draping device according to one embodiment of the present disclosure;

FIG. 9B is another end view of a draping device according to one embodiment of the present disclosure;

FIG. 9C is another end view of a draping device according to one embodiment of the present disclosure;

FIG. 15A is an end view depicting a feature of a draping device according to yet another embodiment;

FIG. 15C is yet another end view depicting a feature of a draping device;

FIG. 22A is a top perspective view depicting one possible use of a draping device according to one embodiment of the present disclosure;

DETAILED DESCRIPTION

Figure 2A:
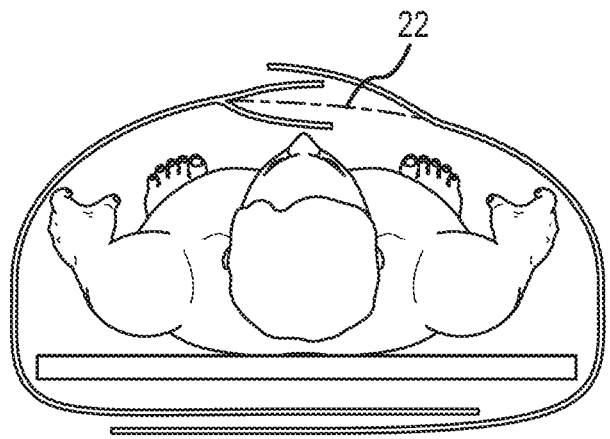
FIG. 2A is an end view of a patient with a draping device according to one embodiment of the present disclosure.
Figure 2B:
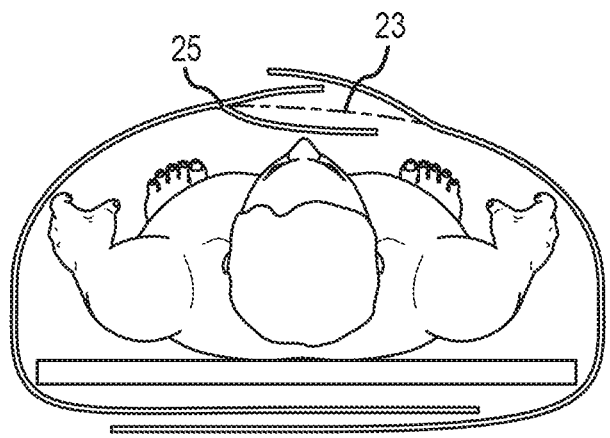
FIG. 2B is another end view of the patient with a draping device according to one embodiment of the present disclosure.
Figure 2C:
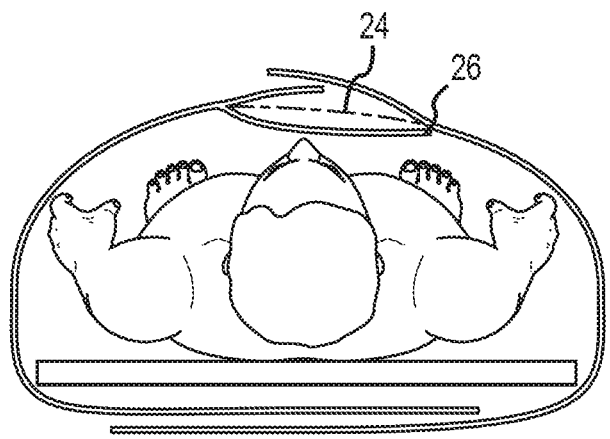
FIG. 2C is another end view of the patient with a draping device according to one embodiment of the present disclosure.

By way of providing additional background, context, and to further satisfy the written description requirements of 35 U.S.C. § 112, the following references are incorporated by reference in their entireties for the express purpose of explaining the nature of the surgical procedures referred to herein and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No.

5,527,312 to Ray; U.S. Patent 6,314,959 to Griesbach et al.; and U.S. Pat. Appl. No. 2008/0255564 to Michelson.

U.S. Patent Publication Nos. 2010/0186754 to Carrez et al. and 2010/0192960 to Rotolo are hereby incorporated by reference in their entireties herein for the express purpose of providing description of various materials and methods of production for surgical drapes.

According to varying embodiments disclosed herein, a draping device and method for using the same is described. As one of or ordinary skill in the art will appreciate, embodiments of the present disclosure may be constructed of materials known to provide, or predictably manufactured to provide the various aspects of the present disclosure. These materials may include, for example, cotton, paper, silk, polyethylene, and polyester. These materials may also include, for example, carbon fiber, ABS plastic, polyurethane, rubber, latex, synthetic rubber, and other fiber-encased resinous materials, synthetic materials, polymers, and natural materials. In another embodiment, some or all elements of the device, or portions of some or all of the elements, are substantially transparent.

Embodiments of the present disclosure present several advantages over the prior art including, for example, the efficacy of the procedure, the sterility of the procedure, the lower risk of infection, etc. Further, the advantages of the device according to various embodiments disclosed herein allows improved viewing of the area intended for surgery. Thus, the presence of one or more transparent areas is one aspect of this disclosure Referring now to FIGS. 1A-14, several embodiments of the present invention are shown. Referring in particular to FIGS. 1A-9C, the drape according to one embodiment (RWD1) has been designed to meet all basic design requirements considered to be mandatory for operating room use. Multiple alternatives are shown for RWD1.

The drape shown in FIGS. 1A-9C, according to varying embodiments, includes a surgical drape, which may be made of a variety of different materials described herein. The surgical drape is of sufficient length and width to encompass a human patient and/or an operating table and associated wires, cables, trays, tools, and instruments, including but not limited to 3D radiographic equipment, which is used during the course of a sterile surgical procedure. The drape according to one embodiment comprises at least one location where the drape is temporarily secured and also provides a sterile field about the at least one longitudinal access, yet may be sterilely separated about this longitudinal access by one of a variety of mechanisms and configurations of the surgical drape. As shown in FIGS. 2A-D this longitudinal sterile separation may be accomplished by a series of overlapping and temporarily attached draping segments (see 4, 6, 8, 10 in FIG. 1C), which is referred to hereinafter as the 'double-underbite' configuration. This double-underbite may further comprise at least one serrated portion of the surgical drape which may become detached by pulling or tearing the surgical drape material at the serrated location. Preferably, as shown in FIG. 1D, this serrated location is not exposed to non-sterile equipment.

FIGS. 1A-1D depict a drape 2 according to one embodiment wherein portions of the drape 2 comprise overlapping features 4, 6, 8, 10 comprising a selectively detachable portion. Overlapping features 4, 6, 8, 10 generally define a sterile area 20 that may be detached in order to remove the drape 2 from a patient and/or workspace.

According to alternate embodiments, this serrated portion of the surgical drape may include serrated portions in multiple locations (see FIG. 2A, 22). In other embodiments, the surgical drape may include at least one zip strip (FIG. 2B, 25) in addition to a serrated portion of the drape (FIG. 2B, 23, FIG. 2C, 24), which may also become separated from the adjoining portion of the surgical drape. According to the embodiment shown in FIG. 2C, the zip strip may be located on an alternative or additional location of the drape relative to the patient (see FIG. 2C, 26).

Other aspects of the invention are shown in FIG. 1C, which includes an under-table wrapping element 12, 14, which is achieved by including fastening devices with each of the overlapping lower portions of the surgical drape 2 where those lower portions overlap 12, 14. A variety of different fastening devices are contemplated for use with the present disclosure, including but not limited to adhesive devices, pins, clips, snaps, hook and loop devices, velcro, magnetic strips, etc.

This design offers navigation readability of a reference frame through sterile overlying plastic cover (or lens), contains an under table wrapping component for easy positioning of 3D radiographic device (or C-arm, O-arm) to and from field, and allows for a simple two step sterile separation of approximated longitudinal sides (e.g. 'underflap' and 'double underbite'). The RWD1 preferably includes a plastic drape and/or has a plastic component (or lens) for navigation readability.

RWD1 variants may comprise transparency to light and/or transmissivity to various known radiographic devices (see FIGS. 1A-4B). For example, the entire drape may be made of transparent and/or translucent plastic. Alternatively, a built-in clear plastic (or other transparent material) section of drape may be provided to allow for readability of the reference frame by navigation technology (see FIGS. 3A-B, ref. no. 30). This plastic section is situated to accommodate for various positions of the reference frame on the patient to include cervical, thoracic, lumbar, as well as bilateral sacroiliac. The plastic region may further accommodate a variety of anatomic placement of the reference frame by one of several mechanisms, by way of example but not limitation: longitudinal sterile separation extending most if not the entire length of the drape.

Figure 3A:
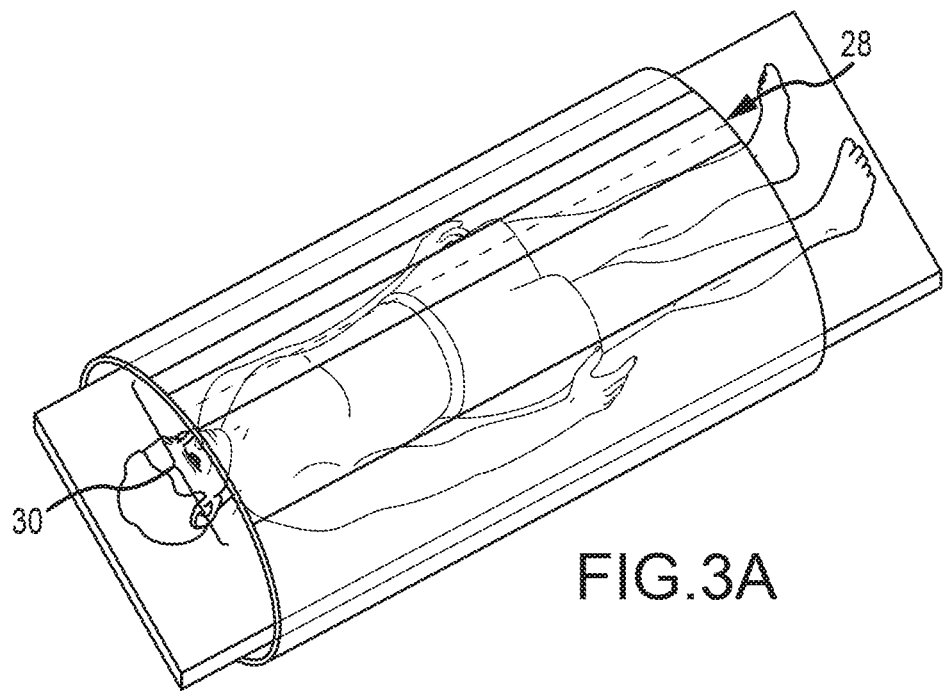
FIG. 3A is a top perspective view of the draping device according to one embodiment of the present disclosure.
Figure 3B:
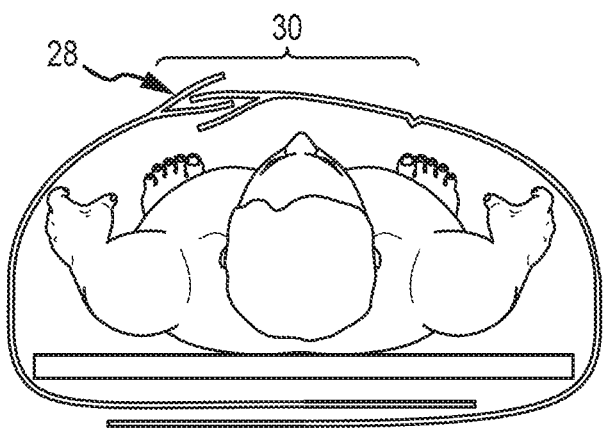
FIG. 3B is an end view of the draping device shown in FIG. 3A.
Figure 4A:
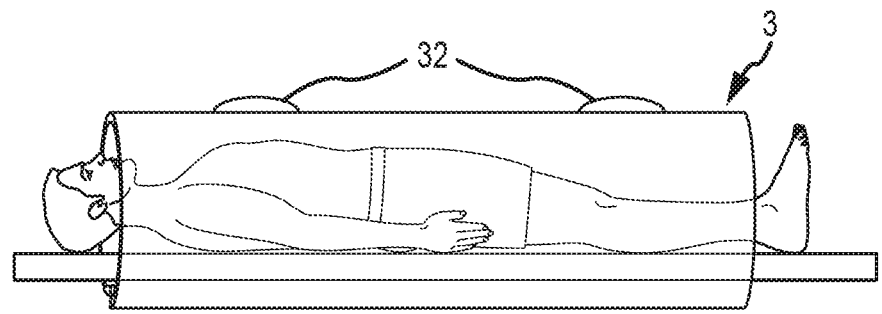
FIG. 4A is a side elevation view of a patient with a draping device according to one embodiment of the present disclosure.
Figure 4B:
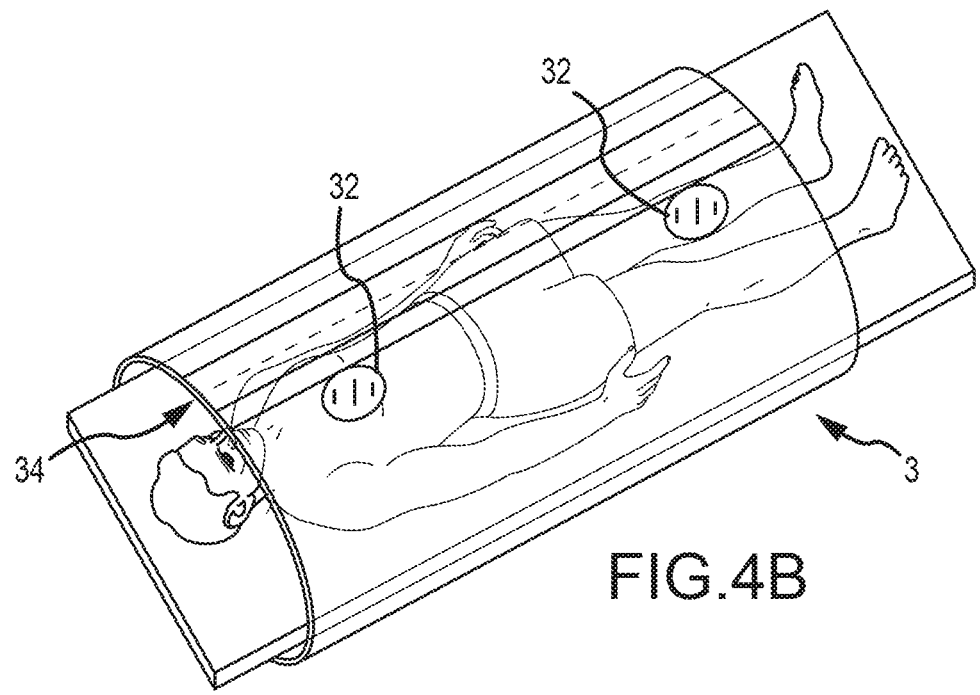
FIG. 4B is a top perspective view of the draping device shown in FIG. 4A.
Figure 5A:
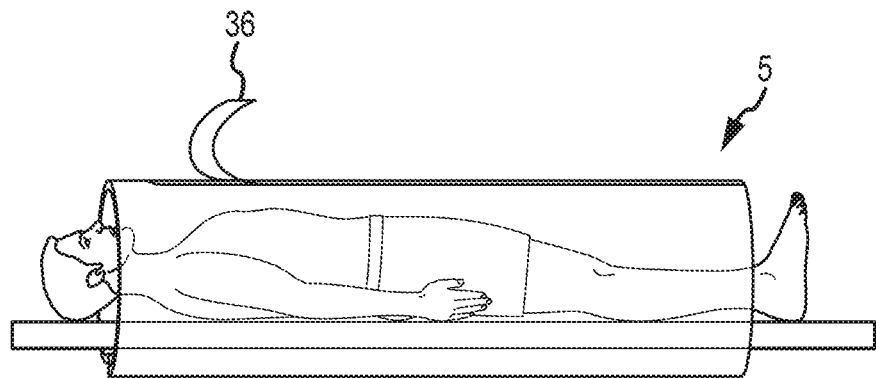
FIG. 5A is a side elevation view of a patient with a draping device according to one embodiment of the present disclosure.
Figure 5B:
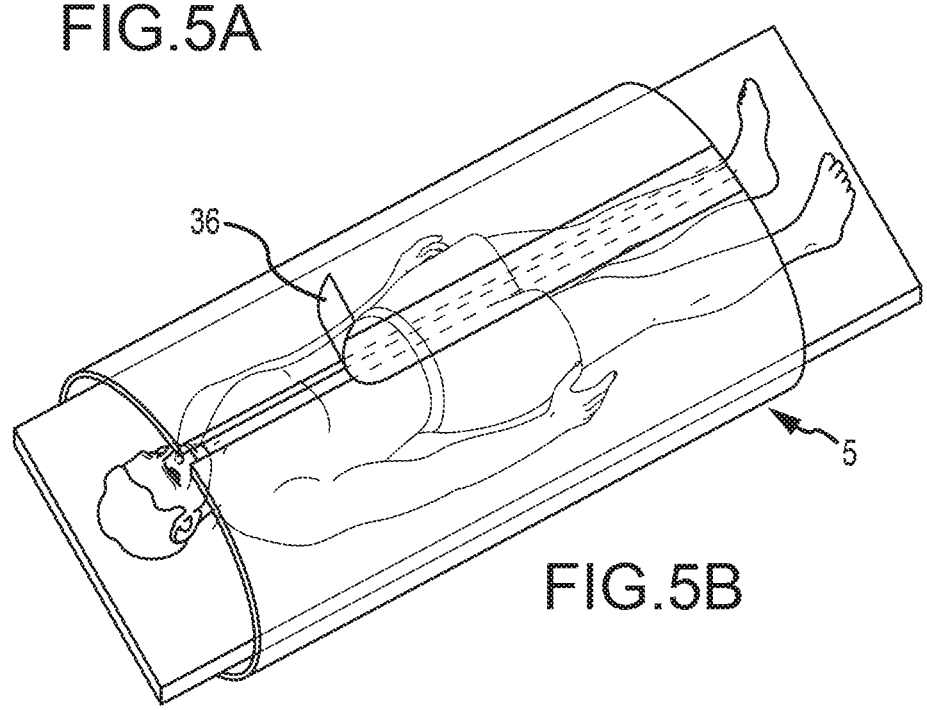
FIG. 5B is a top perspective view of the draping device shown in FIG. 5A.
Figure 5C:
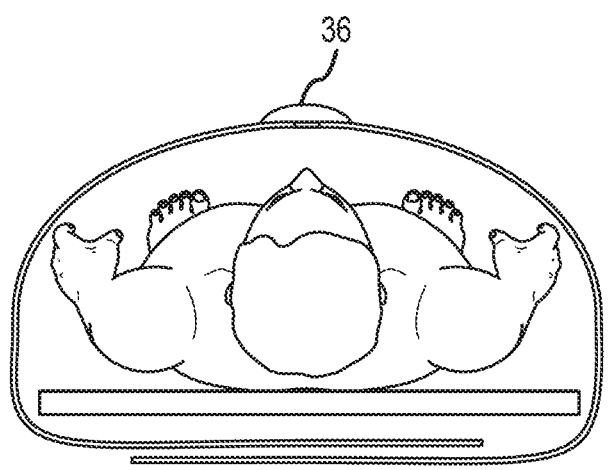
FIG. 5C is an end view of the draping device shown in FIG. 5A.
Figure 7A:
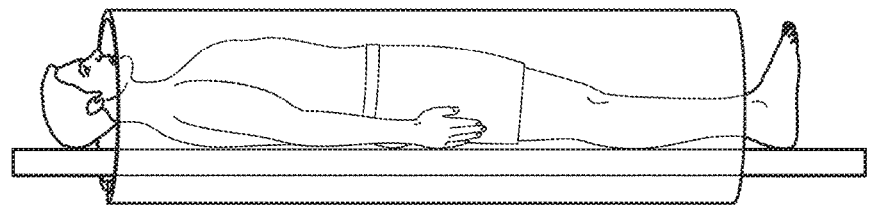
FIG. 7A is a side elevation view of a patient with a draping device according to one embodiment of the present disclosure.
Figure 7B:
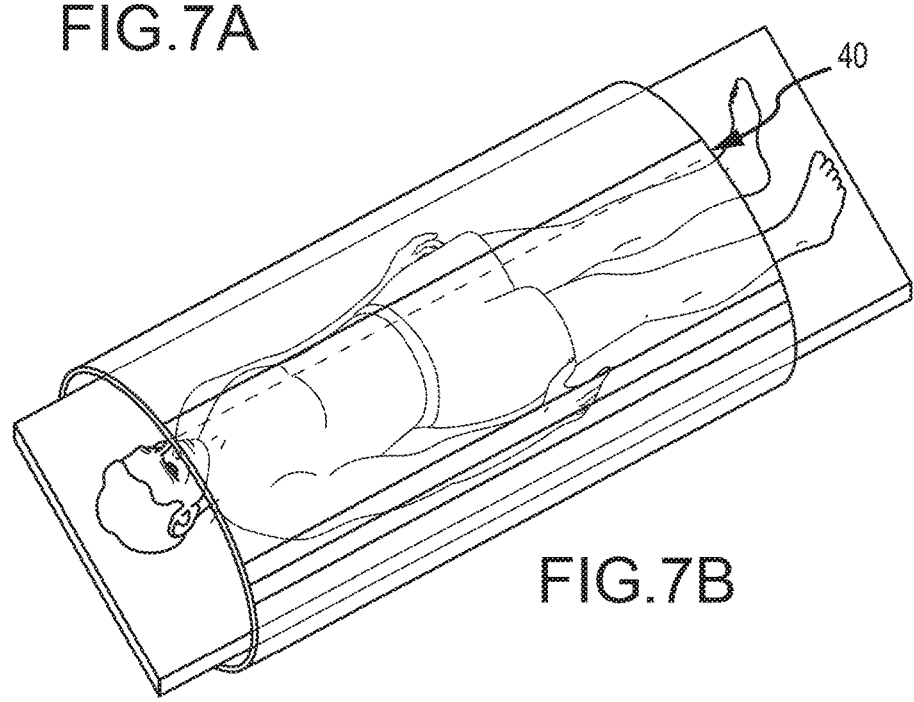
FIG. 7B is a top perspective view of the draping device shown in FIG. 7A.
Figure 7D:
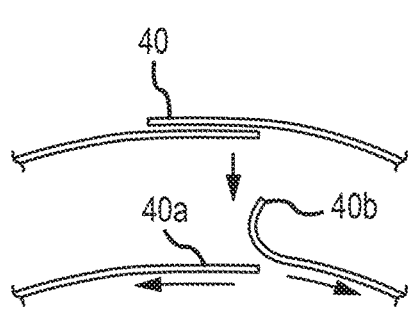
FIG. 7D is a sectional view of the longitudinal sterile separation for the draping device shown in FIG. 7A.
Figure 7C:
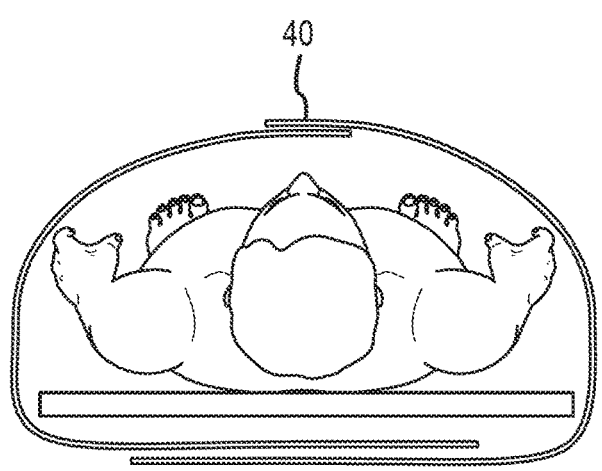
FIG. 7C is an end view of the draping device shown in FIG. 7A.

FIGS. 3A-B depict one embodiment of the drape wherein a separable portion 28 adapted to maintain a sterile field generally extends along a longitudinal length of the drape. A transmissive or translucent portion 30 comprising at least a portion of the width of the drape and extending along the length of the drape is provided. It will be expressly understood that this portion 30 may be of various dimensions and, in alternative embodiments, does not extend along the entire width or length of the drape.

In various embodiments, one or more transparent portions or lenses may be placed at various locations (FIGS. 4A-B, 32) on the drape 3 to accommodate for different anatomic positions. Plastic may be incorporated into just a portion of the drape (either inferior or superior) as shown in FIG. 3B, yet with the ability to reverse the orientation of the drape when placing it thus again accommodating for different anatomic positions. Such concepts also apply when accommodating for use of the reference frame in ENT procedures, brain surgery, and pelvic surgery among other types of surgeries utilizing navigation technology. Although FIGS. 1A-4B are depicted with a 'double underbite' separation, it is expressly understood that any of the other separation designs including but not limited to the 'single-underbite' and 'Z-Shaped' separation designs described herein may be substituted.

Referring to FIGS. 1A-3B, the draping device preferably comprises at least one sterile separation element, which may extend longitudinally the entire or less than the entire length of the draping device. As shown in the Figures, the superior aspect of the separation element falls on the inferior aspect of the separation element, thereby overlapping and protecting the separation seam and the unsterile edge of the draping device from contacting the underlying sterile field.

Sterile separation of longitudinal effaced sides (see FIGS. 1A-8D) provides several advantages: it has the unique ability for the two longitudinally effaced lateral sides to separate and fall away to their ipsilateral side in a simple (one or two step) sterile fashion. Thus, as shown in the appended drawing figures, multiple unique designs for a surgical drape are disclosed that allow preservation of sterile edges of both separating sides, including the 'double underbite' (depicted in FIGS. 1A-4B), 'peel away flap cover' (FIGS. 5A-C, 36), 'single underbite' (FIGS. 6A-C, 38), 'curled lip' (FIGS. 7A-D, 40a, 40b), and 'underflap' (FIGS. 8A-D, 50). Various means of initial connection are utilized, including but not limited to the following: serration, static, tacking, seam weld, zip strip, adhesive, tape/steristrip, among others listed herein.

Figure 8A:
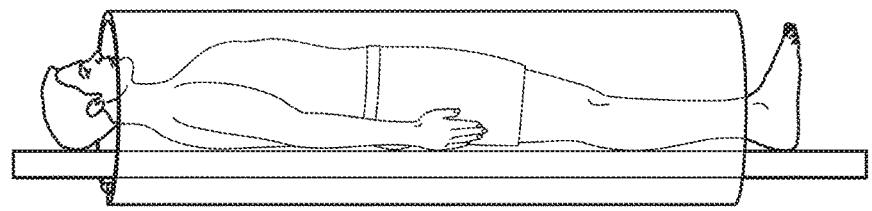
FIG. 8A is a side elevation view of a draping device according to one embodiment of the present disclosure.
Figure 8B:
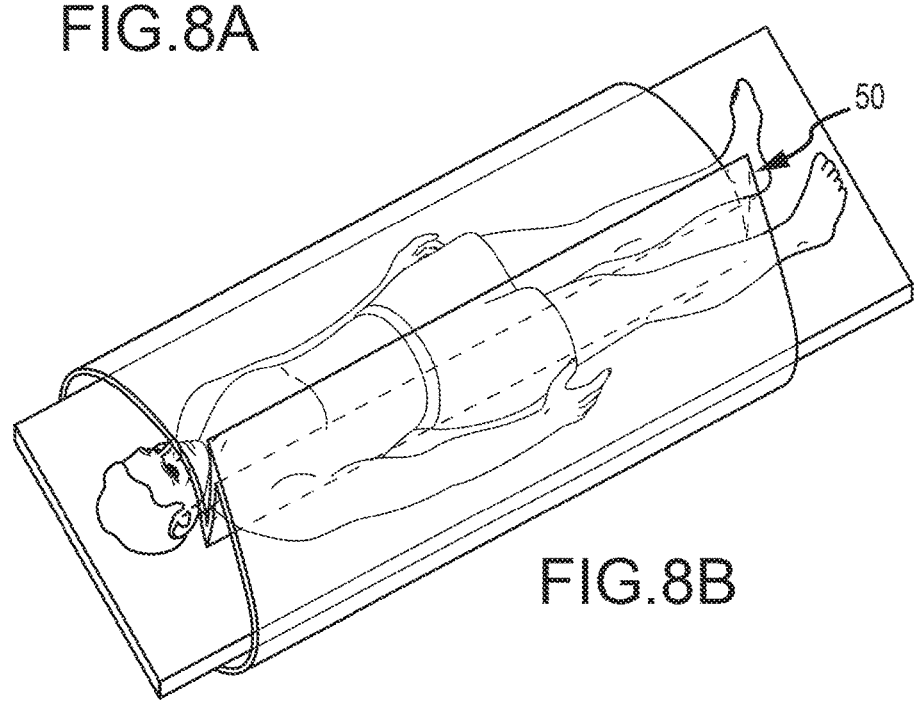
FIG. 8B is a top perspective view of the draping device shown in FIG. 8A.
Figure 8D:
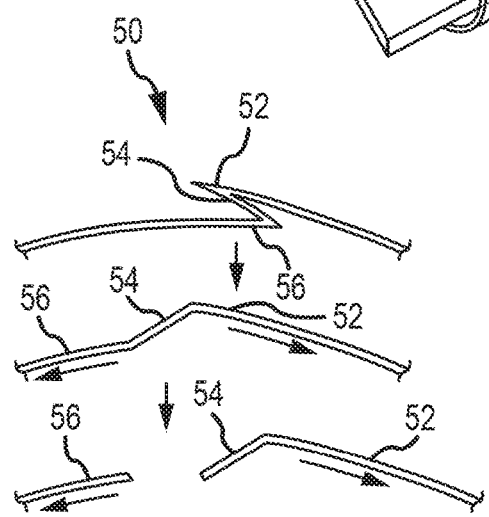
FIG. 8D is a sectional view of the draping device shown in FIG. 8A.
Figure 8C:
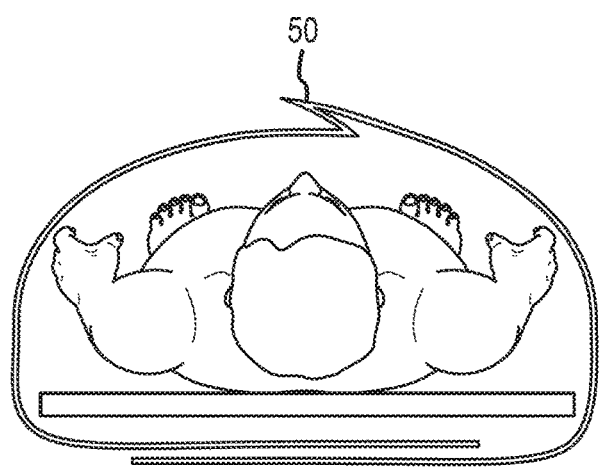
FIG. 8C is an end view of the draping device shown in FIG. 8A.
Figure 10A:
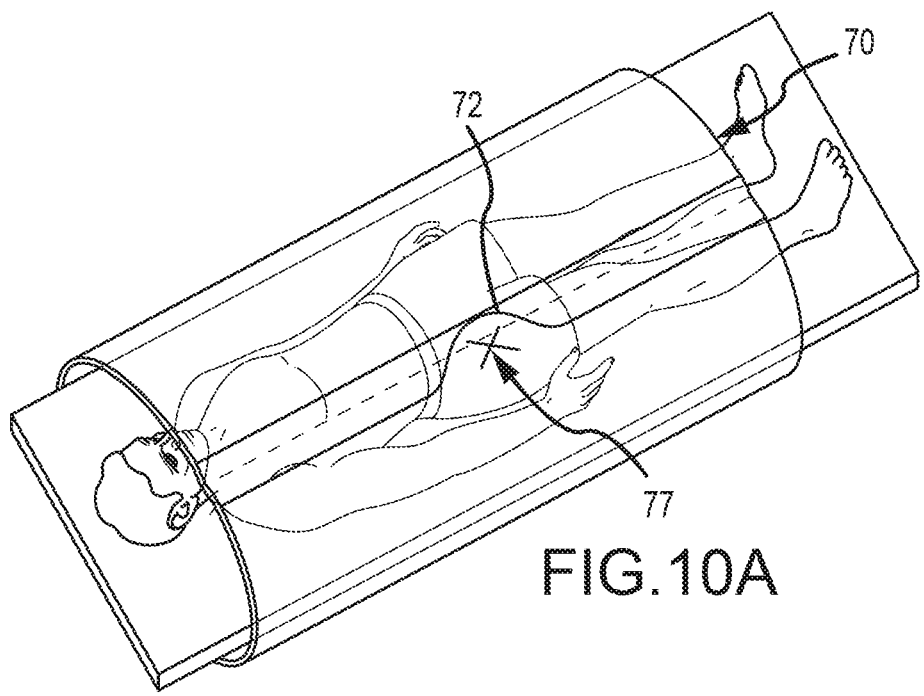
FIG. 10A is a top perspective view of a draping device according to one embodiment of the present disclosure.
Figure 10B:
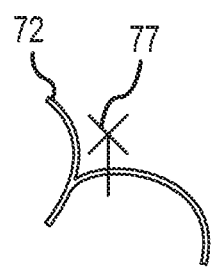
FIG. 10B is an end view of the draping device shown in FIG. 10A.

FIGS. 8A-D depict an embodiment wherein the underflap design 50 is provided. As shown, a separation area may be covered by a pleat 52 which covers and/or protects additional areas of the drape 54, 56 in a first position. The underflap may be opened and separated along a predetermined tear line or separation point as described herein. In at least one embodiment, a longitudinal score line or separation point is disposed below the pleat 52 as shown in FIG. 8D.

The under-table wrapping component (see FIGS. 9A-C) has the following features: each lateral side hanging over the table connects underneath by a variety of means 62 thereby enclosing all hanging wires, catheters, and other medical equipment commonly located under the OR table and at risk of getting 'snagged' by the entering and exiting 3D radiographic device (or C-arm). The two hanging sides 66, 68 of the drape connect under the table by various means 62, including but not limited to the following: velcro, adhesive, static, buttons, cloth (or other material) ties among others. Straps with such connections may further or alternatively be utilized. These various connective possibilities are adjustable and configurable in quantity and location, and thus accommodate for different overall circumferences as table frame size, patient size, and arm positioning all can possibly alter this measurement.

Referring now to FIGS. 10A-13B, another embodiment of the surgical drape (RWD2) has been designed to meet all basic design requirements considered to be mandatory for operating room use. RDW2 variants contain the same essential design characteristics as RWD1 yet adds the ability to provide the surgeon the option of direct exposure of a reference frame 77 (with minimal potential sterility compromise). This specific design provides all three major aspects of RWD1 described above, but provides the option of leaving the frame exposed directly to the navigation device if desired by the surgeon. As shown, a portion 72 of the drape may be gusseted or extended in a manner that allows for selective displacement of the portion 72 without disrupting or contaminating a remainder of the drape. Accordingly, a portion of an underlying patient may be exposed when access is required or desired for various procedures without complete removal of the drape.

As is the case with RWD1, more than one design variant is disclosed below. (See FIGS. 10A-13B). The surgeon may allow for direct exposure after the drape has been placed with complete coverage of the underlying sterile field (as the initial design provides in RWD1). The direct exposure option keeps the underlying field sterile with the only exception being that of the protruding neck and reference frame itself. If the surgeon believes the accuracy of information is comprised by the overlying plastic cover or lens, he/she may decide to utilize this 'direct' option at the slight potential compromise of sterility. The surgeon, if executing this option, still benefits from the temporary sterile coverage of the rest of the field. The under-the-table wrapping feature (to make positioning of the radiographic device safer, quicker, and easier), and the efficiency of the removal process as both sides of the drape seamlessly fall away to their respective sides is further incorporated with the surgical drape in this embodiment.

In the embodiment referred to as RWD2 (as depicted in FIGS. 10A-13B), the reference frame 77 is placed through the drape 70 by separating a small portion 72 of the serrated connection of the two opposing sides. In the 'direct' version (meaning direct visualization of the reference frame by the navigation monitor), the overlying plastic slip 72 is partially pulled back (depicted in FIGS. 10A-11C and 13A-B) or a component of the cover slip is reflected back (depicted in FIG. 12). Given the undraped radiographic device above, there exists a potential breach in sterility and thus this option must be considered in a risk-benefit analysis by the surgeon prior to execution. Under-table or below-patient wrapping features as shown and described herein are also incorporated into various embodiments of the RWD2. As shown and described in FIGS. 9A-C, fasteners 62, 66 may be provided at or near opposing ends of the drape to secure the opposing ends to one another or additional objects. As an upper or patient-side portion of the drape comprises features for separating and/or detaching the drape from a patient, fasteners 62, 66 may be selectively reversible/detachable fasteners, or may permanently affix to one another.

Figure 11A:
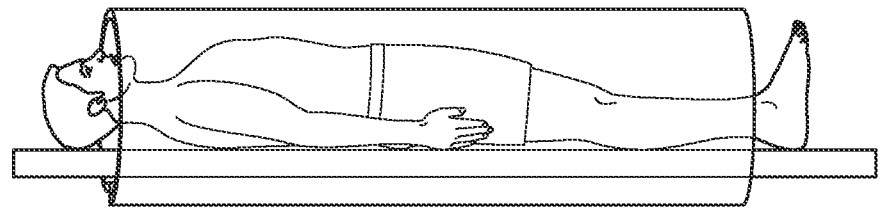
FIG. 11A is a side elevation view of a draping device according to one embodiment of the present disclosure.
Figure 11B:
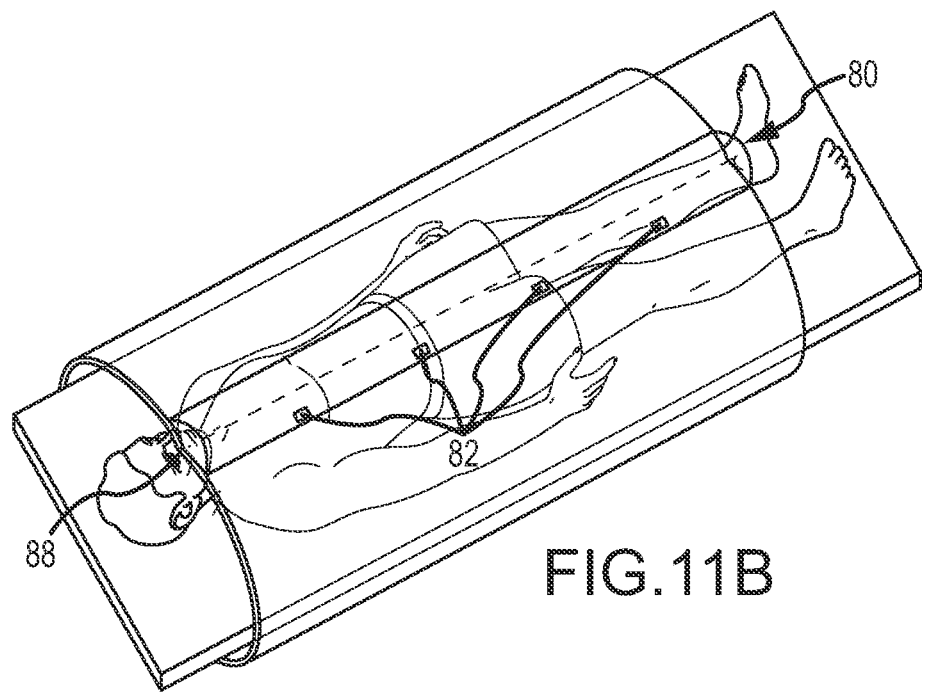
FIG. 11B is a top perspective view of the draping device shown in FIG. 11A.
Figure 11C:
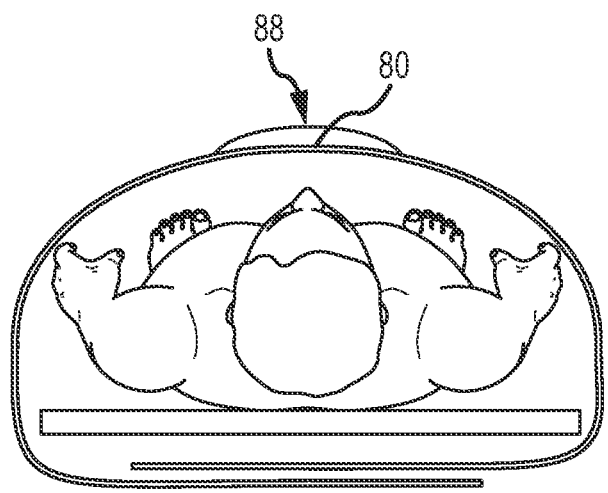
FIG. 11C is an end view of the draping device shown in FIG. 11A.

FIGS. 11A-C depict yet another embodiment of the present invention where one or more fasteners 82 are provided along a longitudinal length of an upper portion of the drape 80. Selectively detachable portions and translucent or transmissive materials 88 may be provided in addition to various fasteners 82.

Figure 12:
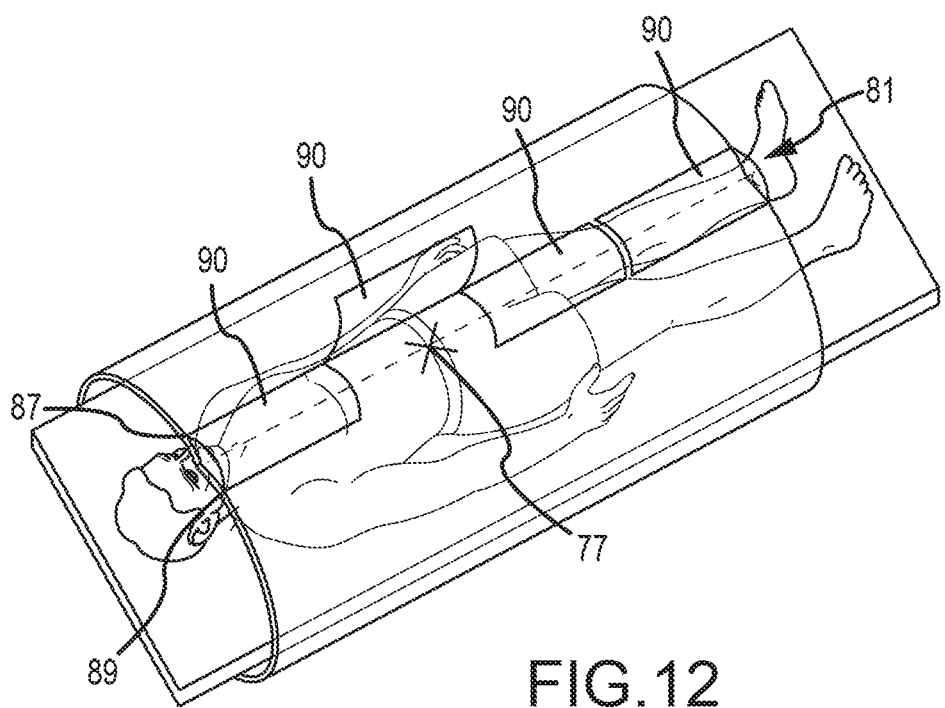
FIG. 12 is a top perspective view of the draping device according to one embodiment of the present disclosure.

FIG. 12 depicts an embodiment of a drape 81 provided with a plurality of hinged portions 90 which allow for selective access to various regions or objects disposed under the drape.

Figure 13A:
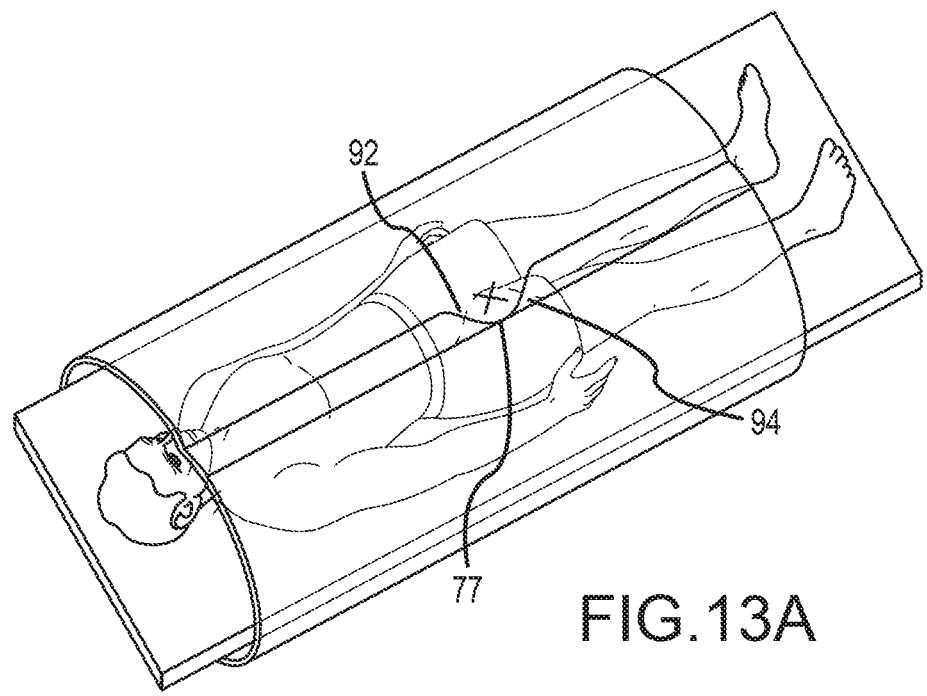
FIG. 13A is a top perspective view of a draping device according to one embodiment of the present disclosure.
Figure 13B:
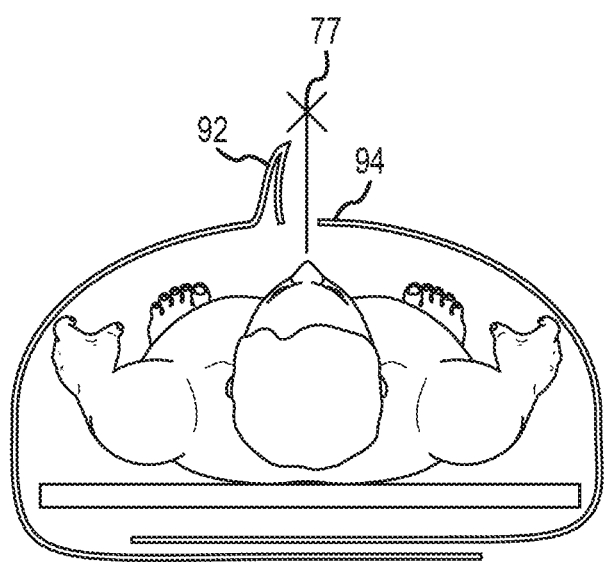
FIG. 13B is an end view of the draping device shown in FIG. 13A.

FIG. 13A-B depict yet another embodiment wherein a hinged portion 92 and corresponding flap 94 are provided for selective access. These features 92, 94 allow for access to a surgical workspace and/or exposure of a reference frame 77.

For the purpose of streamlining the present disclosure, Applicants hereby incorporate by reference U.S. Provisional Patent Application Nos. 61/352,045 and 61/357,637 herein in their entireties. The drape disclosed in these two prior filed provisional patent applications have been designed to meet all basic design requirements considered to be mandatory for operating room use. For those surgeons who remain highly concerned about the potential inaccuracy of the readability of the reference frame by the navigation monitor through a transparent plastic cover or lens for that matter, yet at the same time are unwilling to accept any potential slight breach in sterility (such as in RWD2 where reference frame is left exposed to overlying radiological device as an option), a unique alternate design to address such a concern is provided. This alternate design will be referred to as RWD4.

The RWD4 is a one piece customized disposable surgical drape to be used in any surgery that involves one of the following technologies: (1) stand alone non-draped 3D image acquisition device (requiring greater than 180 degrees of orbital rotation); and (2) image-guided navigation technology. This RWD4 drape accommodates a surgeon's preference, as it allows for both indirect (through plastic or lens) as well as direct navigation readability of the reference frame while the 3D acquisition is taking place.

This drape is different, however, from RWD2 in that in both instances (direct and indirect navigation readability of the reference frame) it maintains sterility of the field to include the protruding reference frame. This drape is modifiable in that the concepts may be adapted to accommodate different anatomical placements of the reference frame and/or various positions of the monitor.

This drape has utility in other surgeries (in addition to spine surgery) such as the pelvic trauma, brain surgery, ENT surgery among others. The 'Frame Hood Cover' is the unique aspect of RWD4 that is designed to cover and protect the reference frame (with attached neck) from the above non-draped (and thus unsterile) 3D radiological device (e.g. O-arm). It is made of a clear, thin plastic to allow navigation readability of the reference frame through the 'Frame Hood Cover' as the 3D data acquisition is taking place. At the same time, it allows for direct and open-air readability by the navigation monitor (rather than through the plastic) in that the 'Frame Hood Cover' is able to be partially open while concomitantly maintaining 'above the reference frame' protection from the directly overlying 3D radiographic device.

Figure 14A:
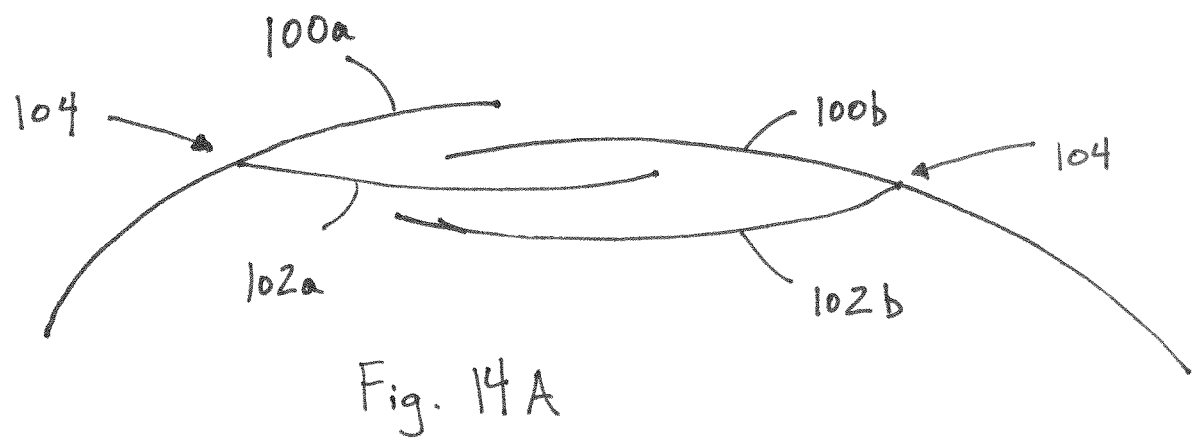
FIG. 14A is an end view depicting a feature of a draping device.
Figure 14B:
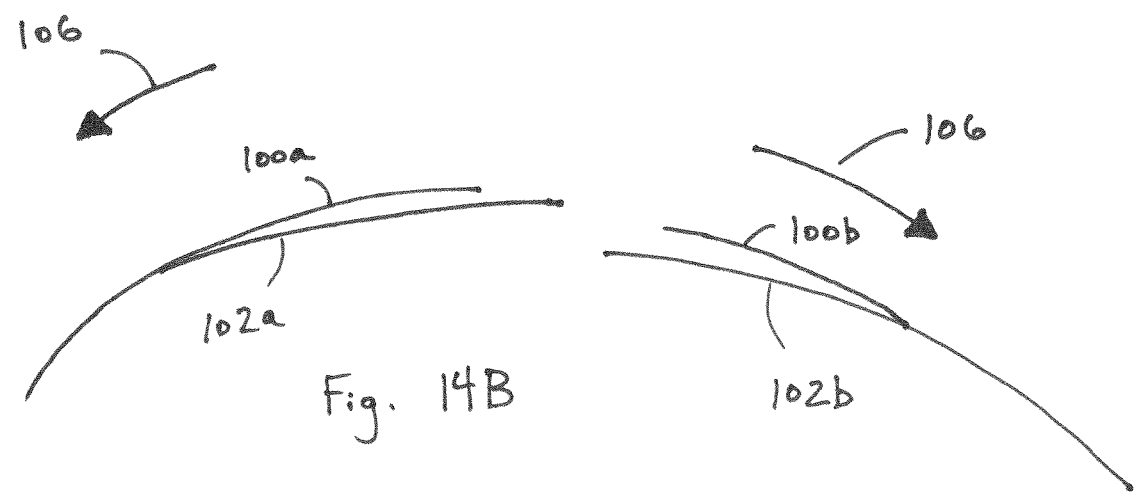
FIG. 14B is an end view depicting a feature of a draping device.

FIGS. 14A-B provide additional end views of yet another sterility maintaining feature that may be employed in various embodiments. As shown, a drape comprises upper 100a and lower 100b superior portions as well as upper 102a and lower 102b inferior portions. One or more separable portions and/or fasteners for securing the drape as described herein and as will be recognized by one of ordinary skill in the art may be provided. The drape may be separable at numerous different locations. For example, separable portion(s) may connect upper superior portion 100a to lower superior portion 100b, lower superior portion 100b to upper inferior portion 102a, upper inferior portion 102a to lower inferior portion 102b, and/or may be connected/provided at the intersections 104 of these features.

When the drape is separated and removed or allowed to fall, upper superior portion 100a will fall to upper inferior portion 102a and lower superior portion 100b will fall to lower inferior portion 102b. Accordingly, superior portions 100a,b which are exposed to various contaminants are prevented from contacting and/or contaminating a patient and/or a workspace by virtue of the dimensions and positioning of the inferior portions 102a,b. As shown, superior portions 100a,b cover the entire surface area of the inferior portions 102a,b in at least a first position of use. Contamination of inferior portions 102a,b from, for example, radiographic and imaging equipment is thus prevented. Upon separation and removal of the drape, contamination of the underlying workspace and/or patient is likewise prevented by inferior portions 102a,b.

FIG. 14B further depicts removal of the drape subsequent to detachment of a selectively securable feature and wherein portions of the drape are transmitted as shown by directional arrows 106. As shown, potentially contaminated upper and lower superior portions 100a,b are prevented from contacting a sterile space by upper and lower inferior portions 102a,b.

FIGS. 15A depicts end views of another sterility-maintaining surgical drape. As shown in FIG. 15A, a portion of the drape comprising a "double Z" flap orientation, which comprises at least one perforation 151 overlying the sterile field. A user applies a pulling force 152 to pull apart the two top portions of the "double Z" flap, and the drape portions separate along the perforation 151. The two halves of the drape may thus be pulled, or allowed to fall, over opposing sides of the sterile field without compromising the sterility of the sterile field. The "double Z" configuration of the drape shown in FIG. 15A maintains a sterile surface adjacent the perforation 151. Although a perforated separable drape is described in these embodiments, it is expressly understood that other means of providing a predetermined separable portion of the drape are included and considered within the scope of the invention. For example, a surface with scoring along the predetermined separable portion may be provided. As another example the drape may be comprised of a different material along the predetermined separable portion, wherein the different material comprises a characteristic which allows it to be torn or separated more easily than the material of the remainder of the drape.

Figure 15B:
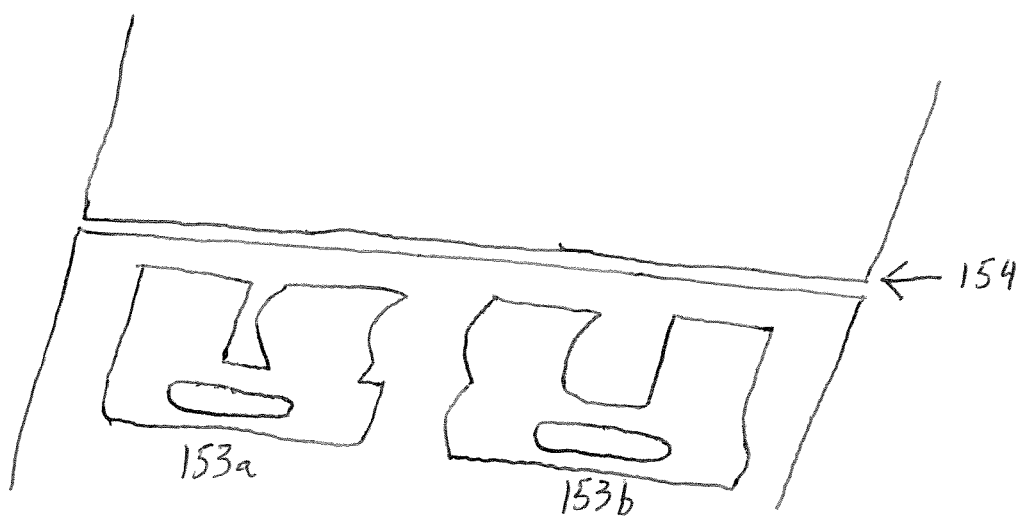
FIG. 15B is another end view depicting a feature of a draping device.

FIGS. 15B and 15C depict a drape with asymmetric handles 153a,b for separating the drape at a drape separation point 154. In the embodiment depicted in FIGS. 15B and 15C, the drape has an outside attachment that is shorter than an inside attachment, resulting in a pulling force 155 applied by a user to be transmitted non-uniformly along a perforation of the drape. In particular, when the user applies the pulling force 155, the outer edges of the drape separate first, creating a necking 156. As the user continues to apply the pulling force 155, the inner portion of the drape further separates until the drape is fully separated.

The embodiments shown in FIGS. 15A-15C may be particularly employed to maintain the sterility of a surgical "back table" and the instruments and equipment lying thereon. The drape may include a separable portion located in a medial section of the "double Z" configuration, or alternatively the separable portion may be located at the seam or transition point or either of the "double Z" folds of the drape shown in FIGS. 15A-C.

Figure 16:
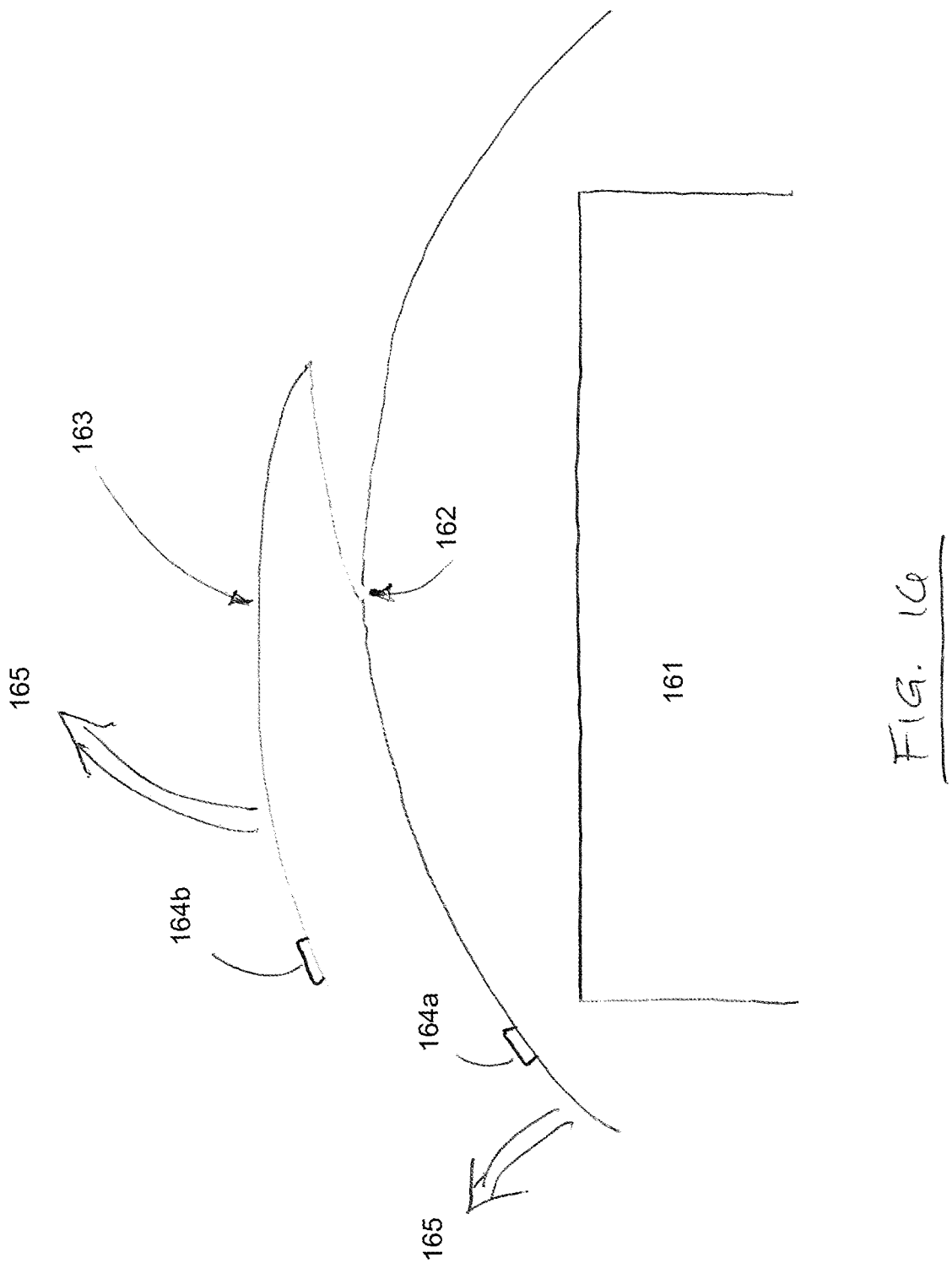
FIG. 16 is an end view depicting one possible use of a draping device according to one embodiment of the present disclosure.

FIG. 16 depicts an end view of another drape, which preferably may be used to maintain the sterility of a surgical back table 161. In this embodiment, the drape comprises a perforated portion 162, which is preferably provided with a superior cover or "dust cover" 163 to an inferior cover. The superior cover 163 and inferior cover preferably comprise handles 164a,b accessible on the same side of the table 161. When the drape is to be removed, a user applies a pulling force 165 to the handles 164a,b to pull the handles toward opposite sides of the table 161 or other sterile underlying surface. The drape separates along the perforated portion 162 and may be pulled, or allowed to fall, over opposing sides of the table 161 without compromising the sterility of the back table 161 or the instruments and equipment thereon. Although handles are described, other mechanisms may be provided for ease of separation and to prevent forces being imparted on the drape in a direction other than the direction required to cause separation of the drape shown in FIG. 16.

In one embodiment, the "dust cover" further comprises one or more handles for ease of use in separating "dust cover." In one embodiment, the "dust cover" may be selectively removable without separating the underlying drape. In yet another embodiment, the act of separating dust cover from drape in turn causes drape to be separated along a predetermined separable portion.

In one embodiment, the handles may be positioned and oriented such that separation first occurs about an outer edge of the drape, as depicted in FIG. 16. In one particular embodiment, the handles may not be symmetrical, and in a preferred embodiment as asymmetrical. These embodiments permit both temporary separation of an outer portion of drape, and also ensure that the separable portions of drape are continually removed away from the underlying sterile field while the remainder of the predetermined separable portion of drape is in the process of separation. As the user continues to pull on the asymmetric handles, the drape will continue to separate from the outer edge to an inner portion of the predetermined separable portion of drape.

Figure 17:
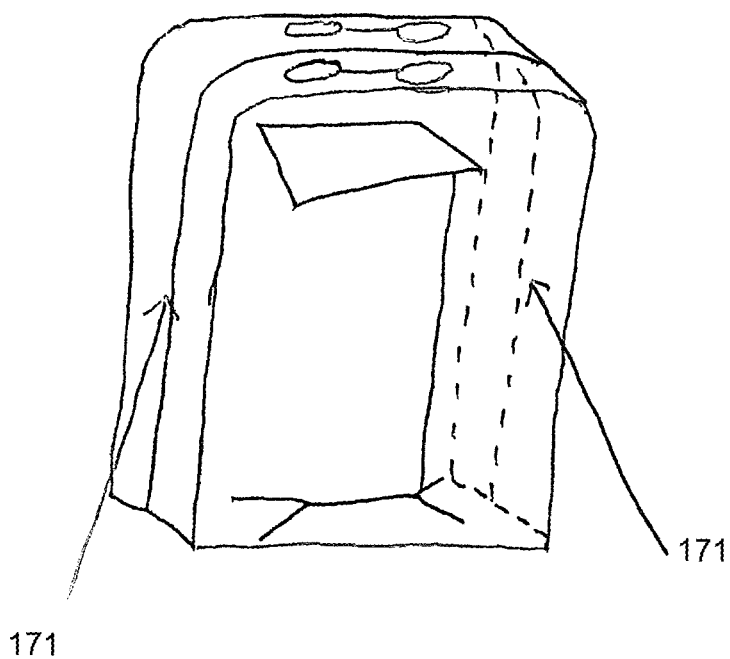
FIG. 17 is a side elevation view depicting a feature of a draping device according to one embodiment of the present disclosure.

FIG. 17 depicts an embodiment of a drape which may be used to cover a movable or repositionable instrument stand, commonly referred to as a "mayo stand," and maintain the sterility of the mayo stand. In this embodiment, the drape comprises a perforated flap 171 along the vertical faces. As shown, the drape of this embodiment further comprises handles in the top face. When the drape is to be removed, the handles are pulled in opposite directions. The drape separates along the perforated flap 171 and may be pulled, or allowed to fall, over the mayo stand without compromising the sterility of the stand or the instruments and equipment thereon. Although handles are described, other mechanisms may be provided for ease of separation and to prevent forces being imparted on the drape in a direction other than the direction required to cause separation of the drape shown in FIG. 17.

Figure 18A:
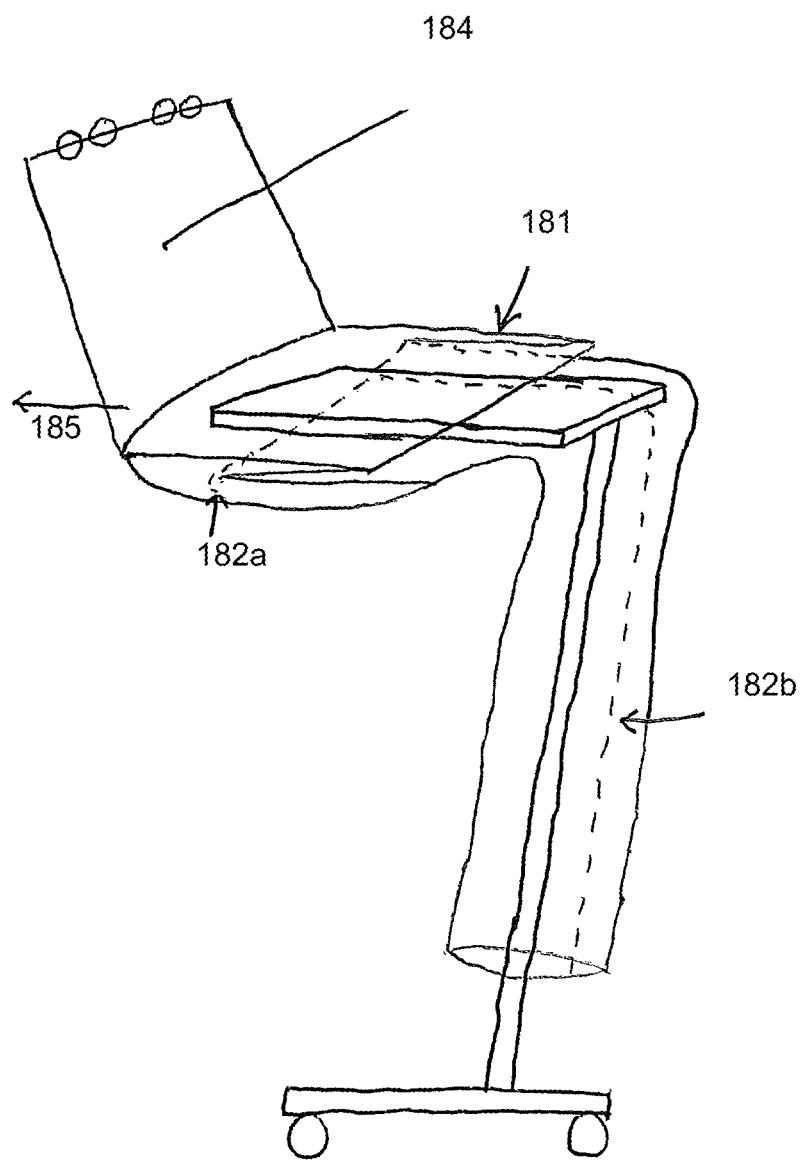
FIG. 18A is a side elevation view depicting one possible use of a draping device according to one embodiment of the present disclosure.
Figure 18B:
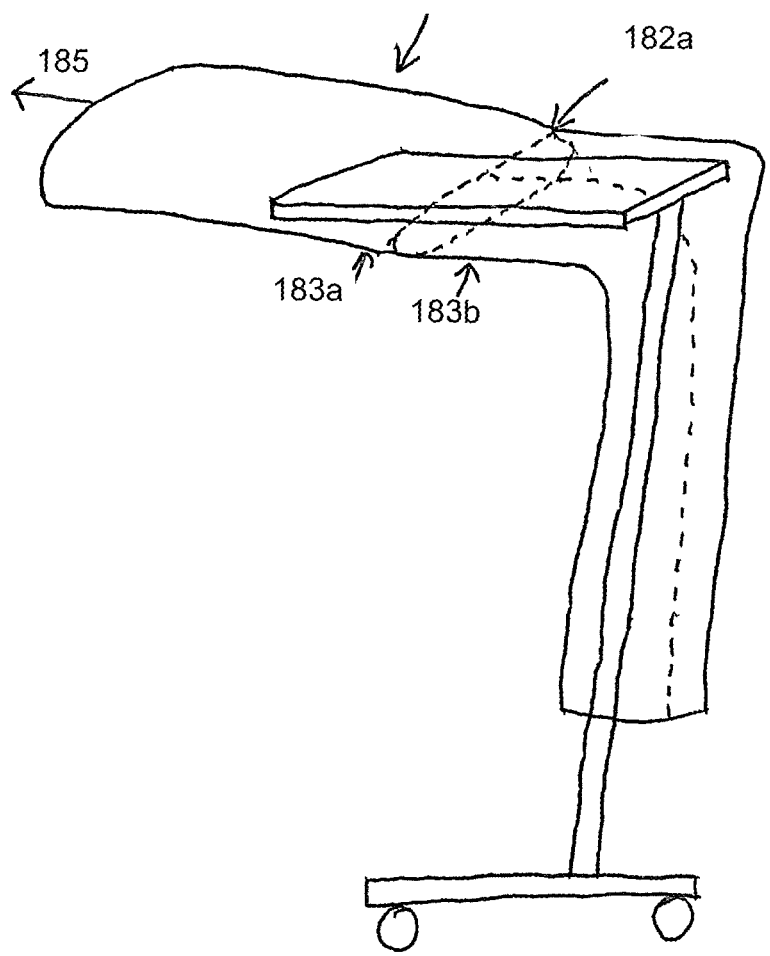
FIG. 18B is another side elevation view depicting one possible use of a draping device according to one embodiment of the present disclosure.
Figure 18C:
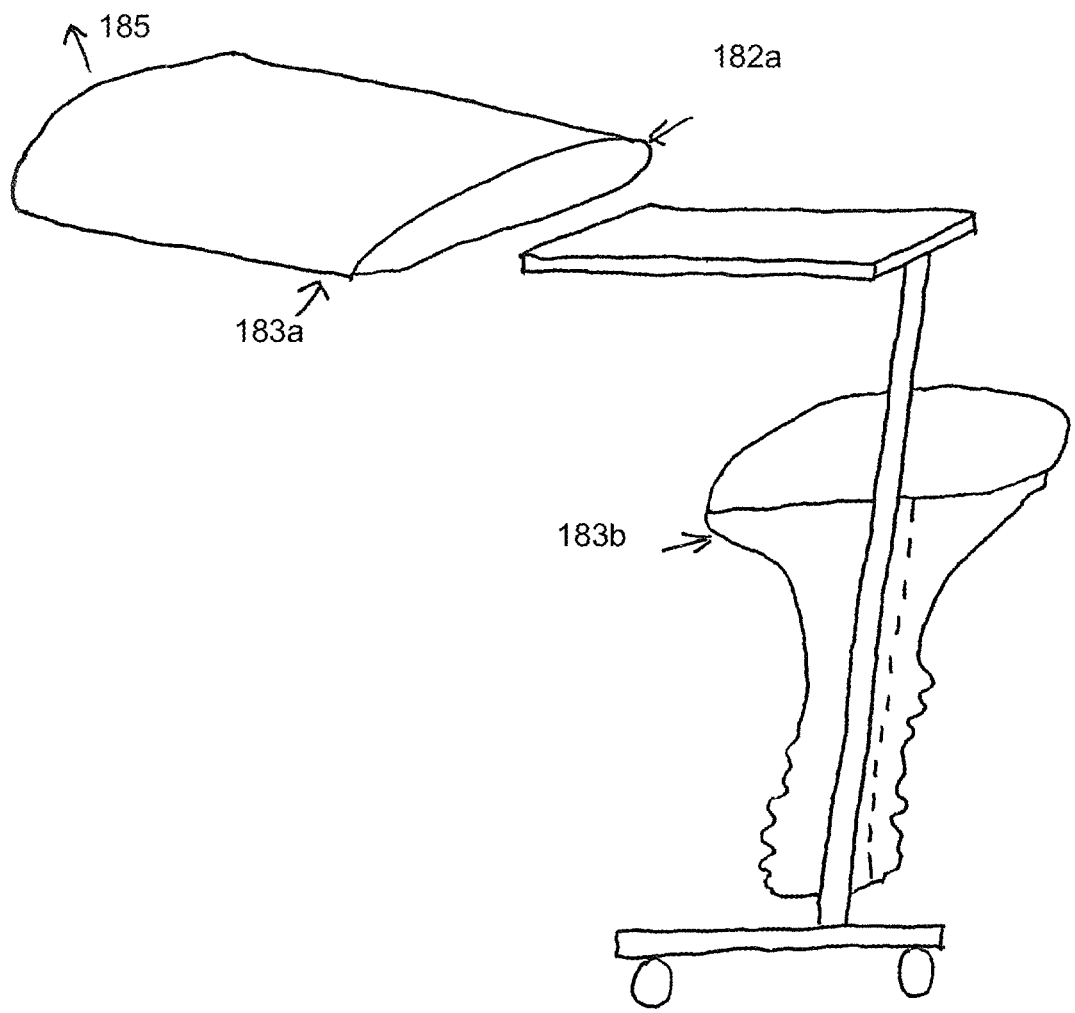
FIG. 18C is another side elevation view depicting one possible use of a draping device according to one embodiment of the present disclosure.
Figure 18D:
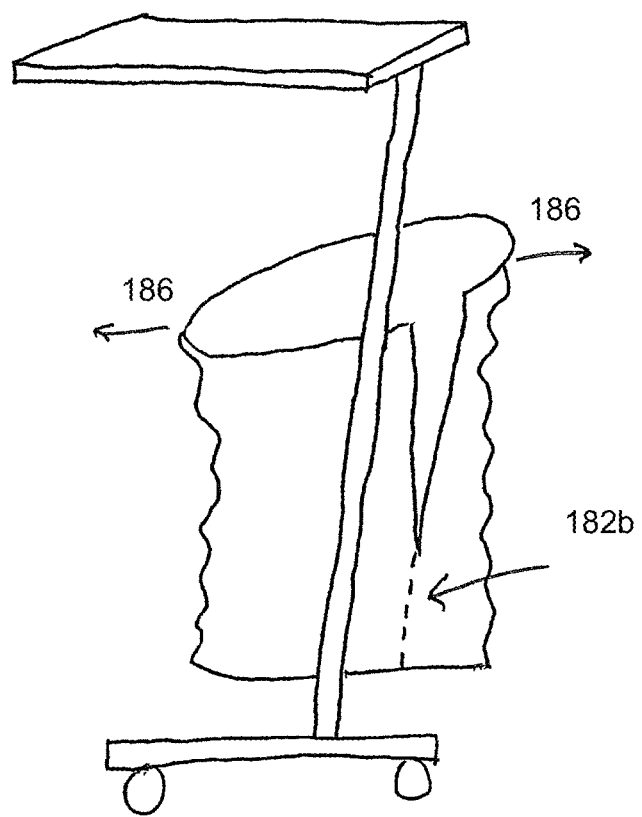
FIG. 18D is another side elevation view depicting one possible use of a draping device according to one embodiment of the present disclosure.

FIGS. 18A-D depict side elevation views of another drape for maintaining the sterility of a mayo stand. A portion of the drape comprises a flap 181, which comprises a breakaway perforation 182a which overlies the top surface of the mayo stand and joins edges of two separable portions of the drape 183a,b. The flap surrounds a table portion of the mayo stand, maintaining the sterility of that portion and the tools and instruments thereon. The drape further comprises other breakaway perforations 182b and a dust cover 184, which, in FIG. 18A, has been pulled up by a user applying a pulling force 185. In FIG. 18B, the flap 181 is pulled straight by the pulling force 185, placing tension on the breakaway perforation 182a of the flap, and, as shown in FIG. 18C, the drape portions separate along the perforation between the separable portions 183a,b. The lower portion of the drape "falls away" without compromising the sterility of the table portion of the mayo stand. The flap 181 maintains a sterile surface adjacent the perforation 182a. As shown in FIG. 18D, the other breakaway perforations 182b on the lower portion of the drape may allow a user to "unzip" the lower portion of the drape by applying a pulling force 186, facilitating easier removal and disposal of the drape. Although a perforated separable drape is described in these embodiments, it is expressly understood that other means of providing a predetermined separable portion of the drape are included and considered within the scope of the invention. For example, a surface with scoring along the predetermined separable portion may be provided. As another example the drape may be comprised of a different material along the predetermined separable portion, wherein the different material comprises a characteristic which allows it to be torn or separated more easily than the material of the remainder of the drape.

Figure 19:
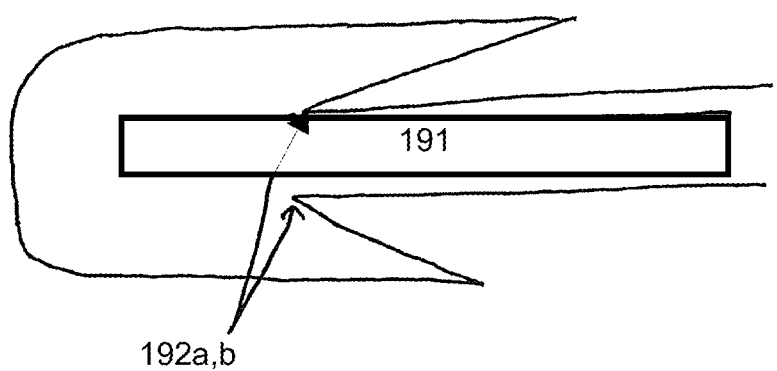
FIG. 19 is a side elevation view depicting a feature of a draping device according to one embodiment of the present disclosure.

FIG. 19 depicts a side elevation view of a drape for maintaining the sterility of a mayo stand. In this embodiment, the drape comprises a Z flap, which surrounds a table portion 191 of the mayo stand circumferentially. Perforations 192a,b on inner portions of the Z flap allow the drape to be separated when the Z flap is pulled straight, as depicted in FIG. 18B.

Figure 20A:
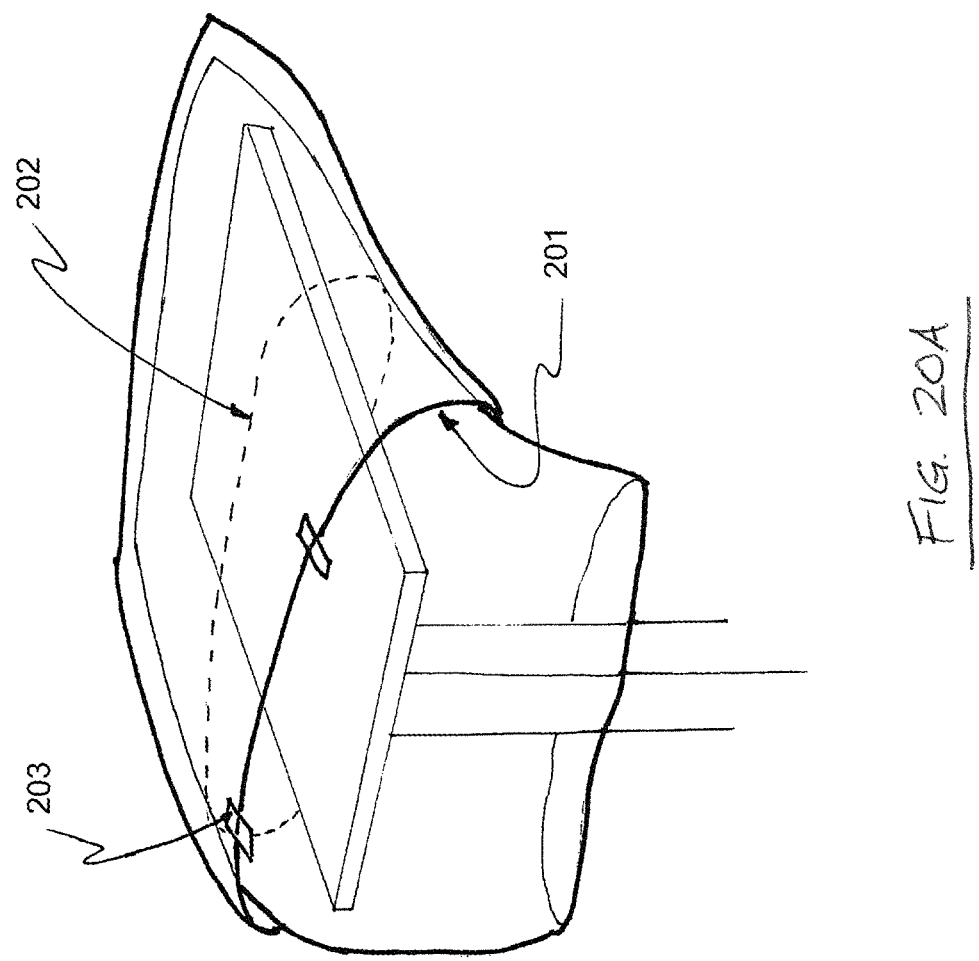
FIG. 20A is a top perspective view depicting one possible use of a draping device according to one embodiment of the present disclosure.
Figure 20B:
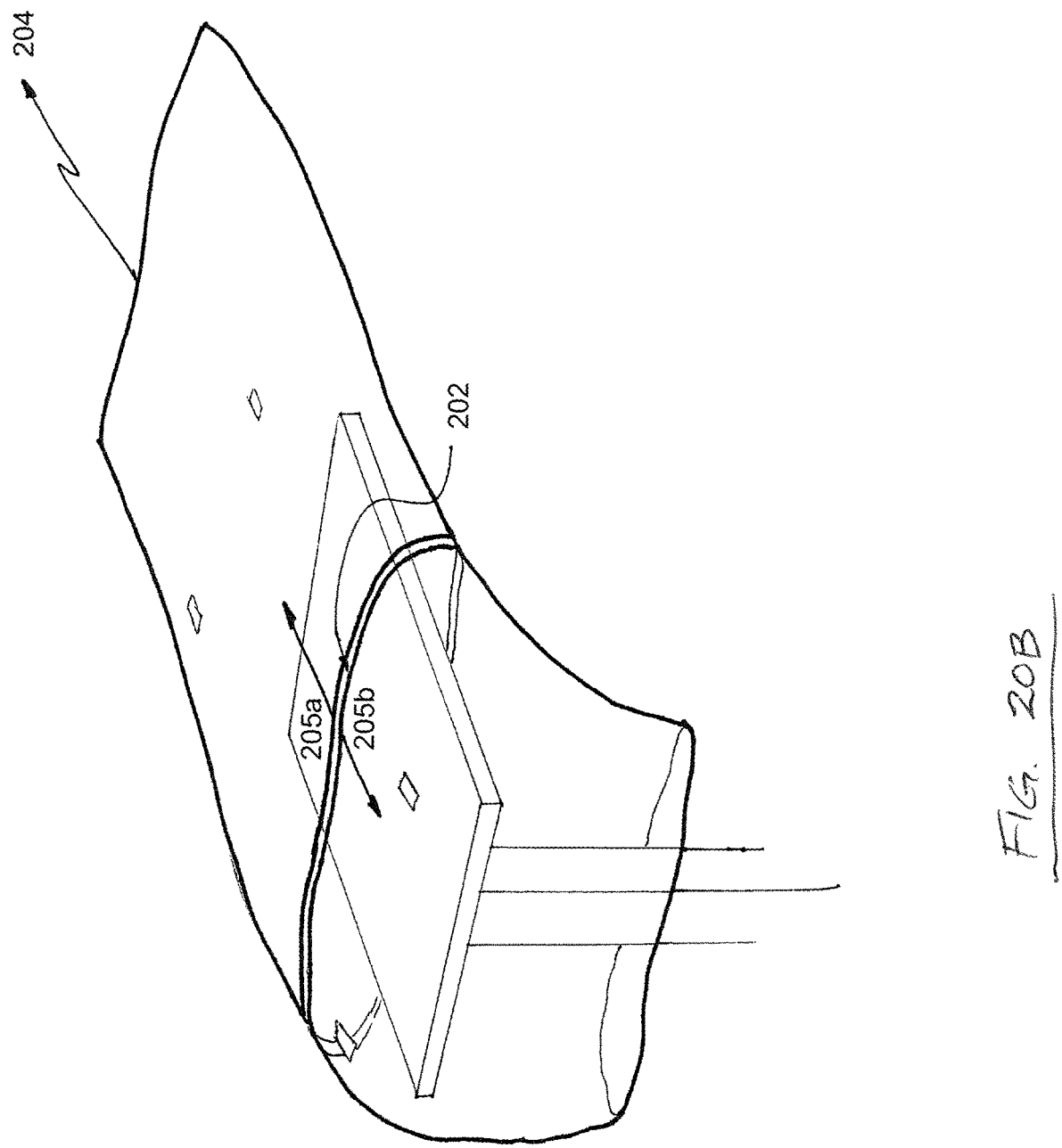
FIG. 20B is another top perspective view depicting one possible use of a draping device according to one embodiment of the present disclosure.

FIGS. 20A and 20B depict top perspective views of another drape for maintaining the sterility of a mayo stand.

As shown in FIG. 20A, the drape comprises a telescope fold 201, which covers a perforation 202 overlying a table portion of a mayo stand. The telescope fold is held in place by at least one "tear here" label 203. As shown in FIG. 20B, the distal end of the drape is pulled outward by a user applying a pulling force 204, breaking the "tear here" labels 203 and unfolding the telescope fold 201. Separable portions 205a,b of the drape then separate along the perforation 202.

Figure 21A:
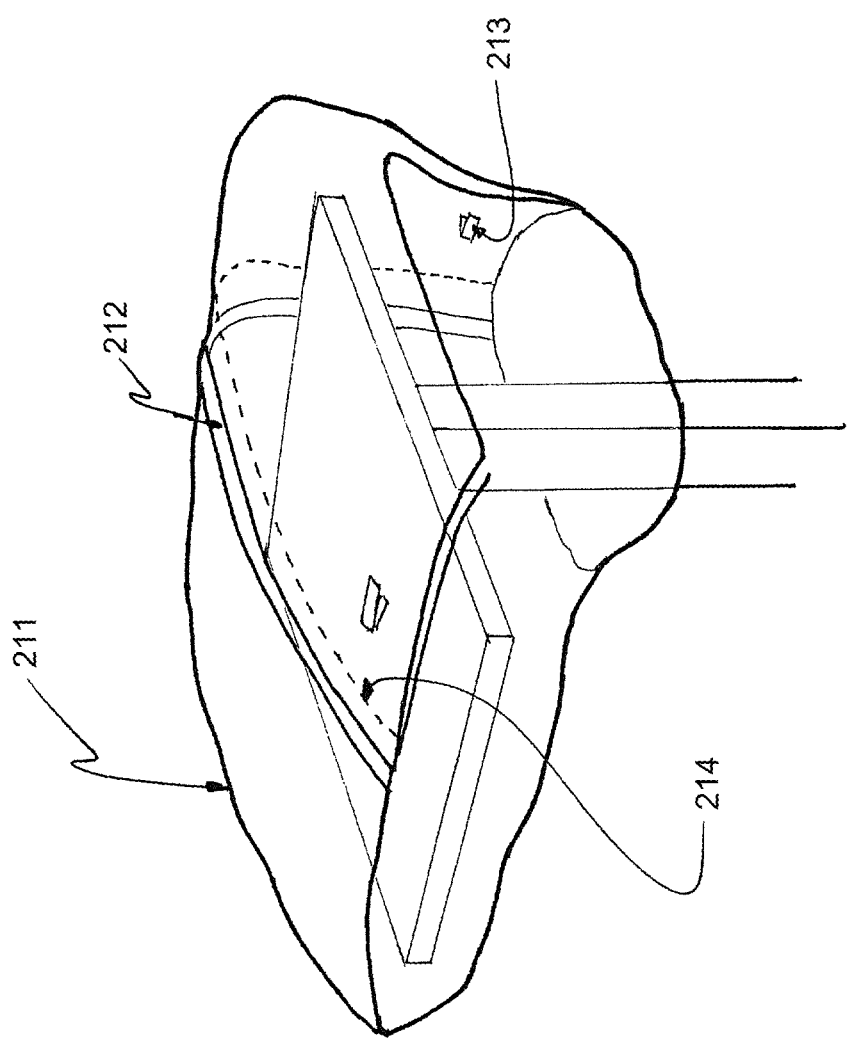
FIG. 21A is a top perspective view depicting one possible use of a draping device according to one embodiment of the present disclosure.
Figure 21B:
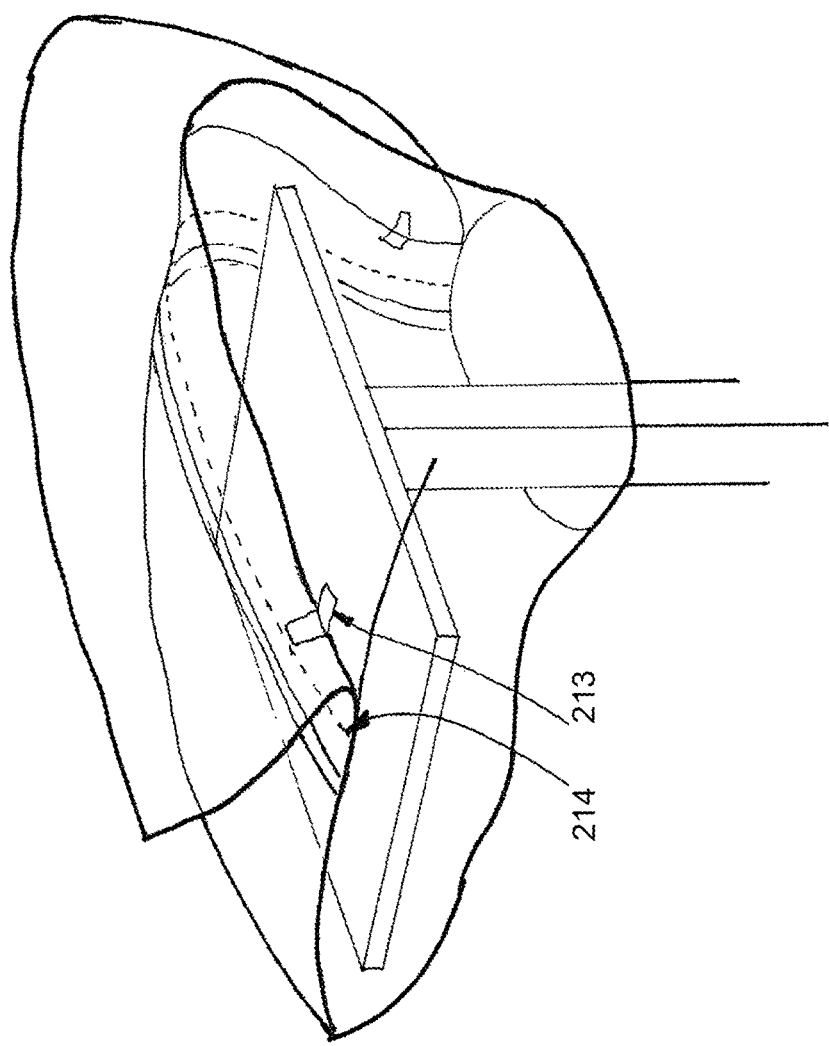
FIG. 21B is another top perspective view depicting one possible use of a draping device according to one embodiment of the present disclosure.
Figure 21C:
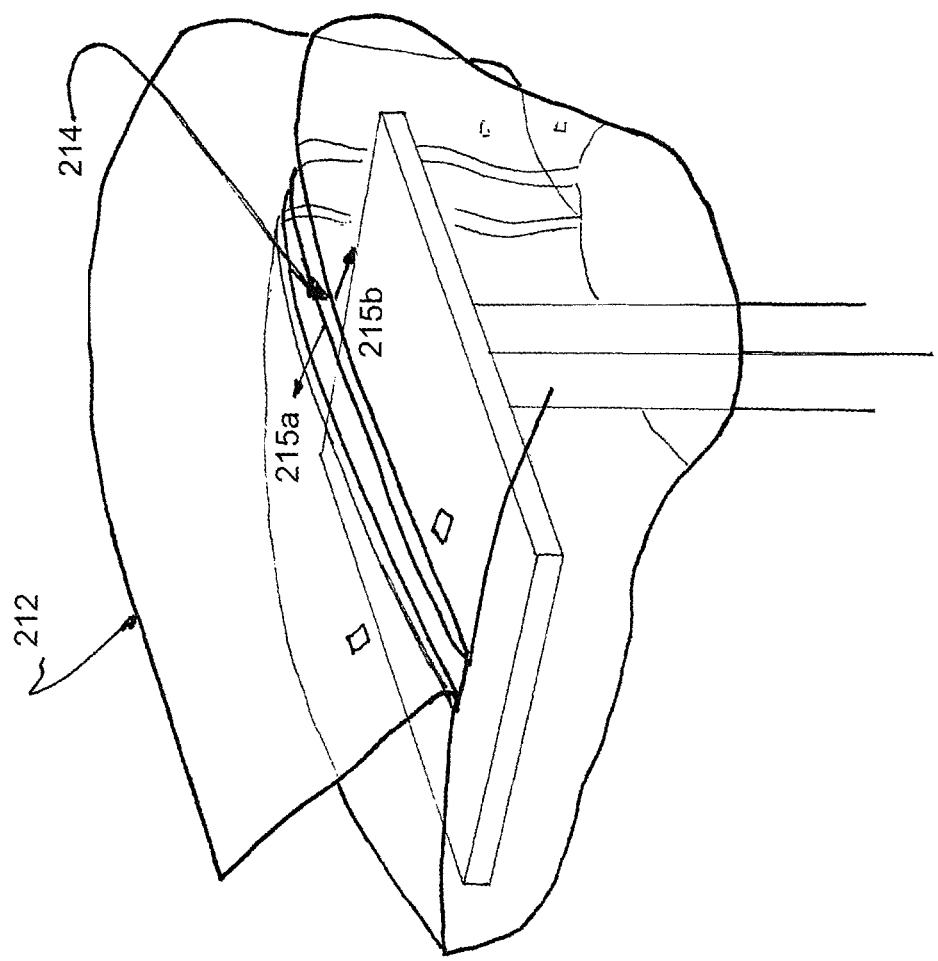
FIG. 21C is another top perspective view depicting one possible use of a draping device according to one embodiment of the present disclosure.

FIGS. 21A-C depict top perspective views of another drape 211 for maintaining the sterility of a mayo stand. As shown in FIG. 21A, the drape 211 is placed over the top surface of a mayo stand and comprises a sealed flap 212, which is held in place by at least one "tear here" label 213. The drape 211 further comprises a perforation 214, which is covered by the flap 212. As shown in FIG. 21B, the "tear here" labels 213 hold the flap 212 in place when the flap 212 is put in light tension, preventing the perforation 214 from being exposed and opening accidentally or prematurely. As shown in FIG. 21C, a greater degree of tension on the flap 212 breaks the "tear here" labels 213 and separates separable portions 215a,b along the perforation 214.

Figure 22B:
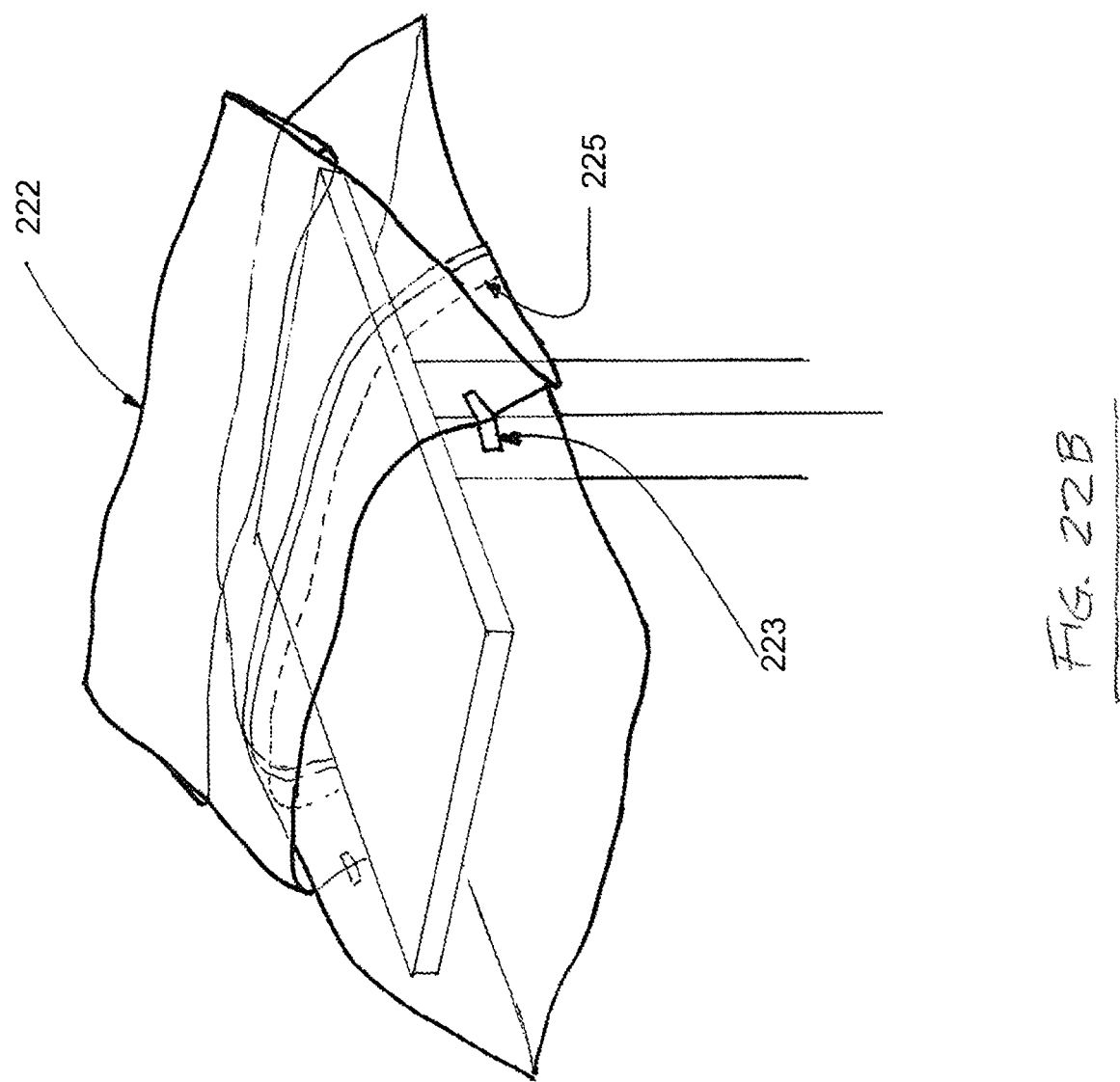
FIG. 22B is another top perspective view depicting one possible use of a draping device according to one embodiment of the present disclosure.
Figure 22C:
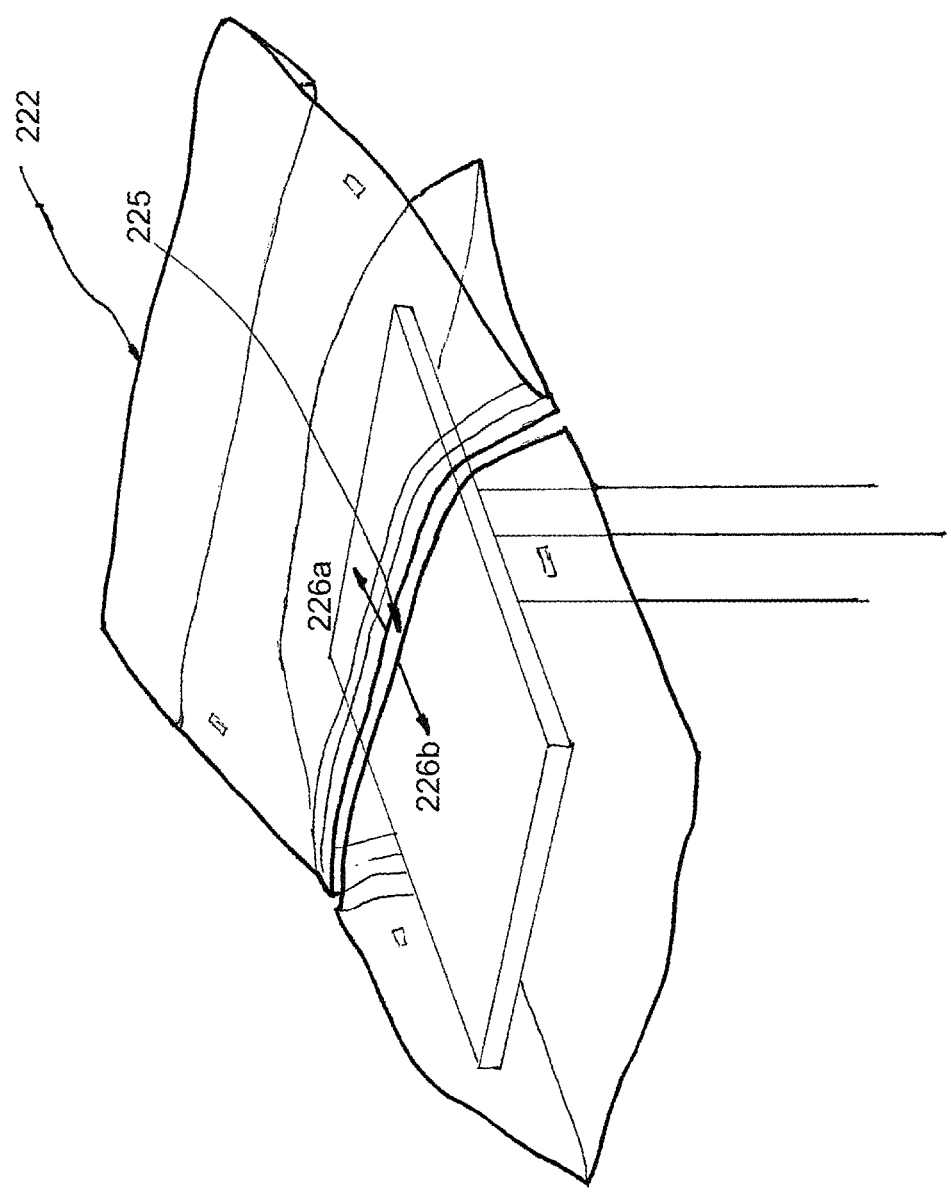
FIG. 22C is another top perspective view depicting one possible use of a draping device according to one embodiment of the present disclosure.

FIGS. 22A-C depict top perspective views of another drape 221 for maintaining the sterility of a mayo stand. As shown in FIG. 22A, the drape 221 is placed over the top surface of a mayo stand and comprises a sealed flap 222, which is held in place by at least one "tear here" label 223 and comprises a cuff end fold 224. The drape 221 further comprises a perforation 225, which is covered by the flap 222. As shown in FIG. 21B, the "tear here" labels 223 hold the flap 222 in place when the flap 222 is put in light tension, preventing the perforation 225 from being exposed and opening accidentally or prematurely. As shown in FIG. 22C, a greater degree of tension on the flap 222 breaks the "tear here" labels 223 and separates separable portions 226a,b along the perforation 225.

Figure 23A:
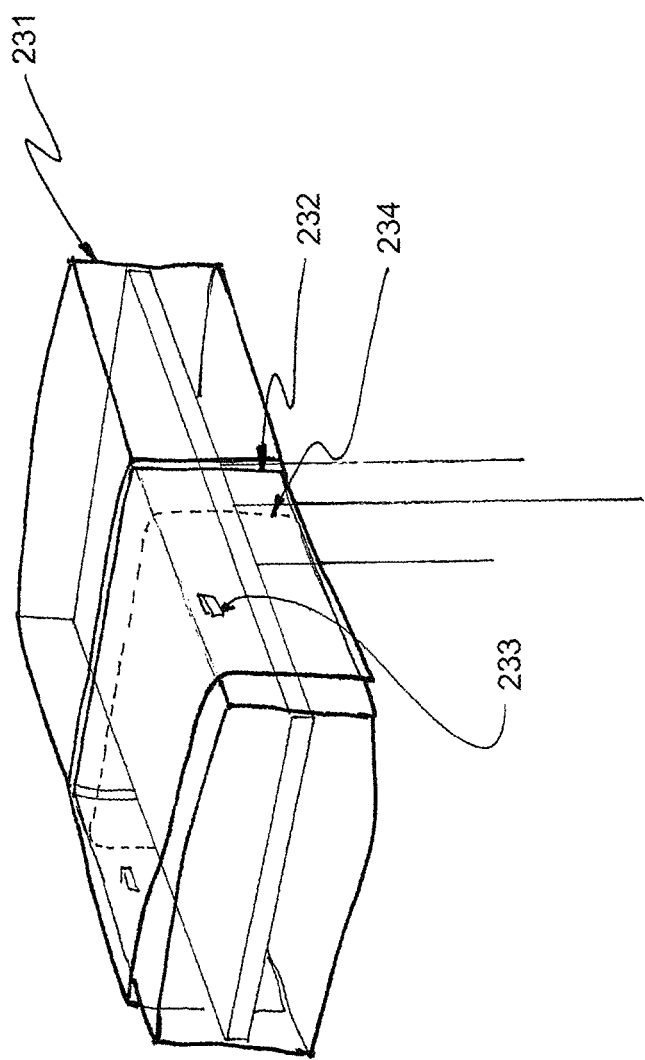
FIG. 23A is a top perspective view depicting one possible use of a draping device according to one embodiment of the present disclosure.
Figure 23B:
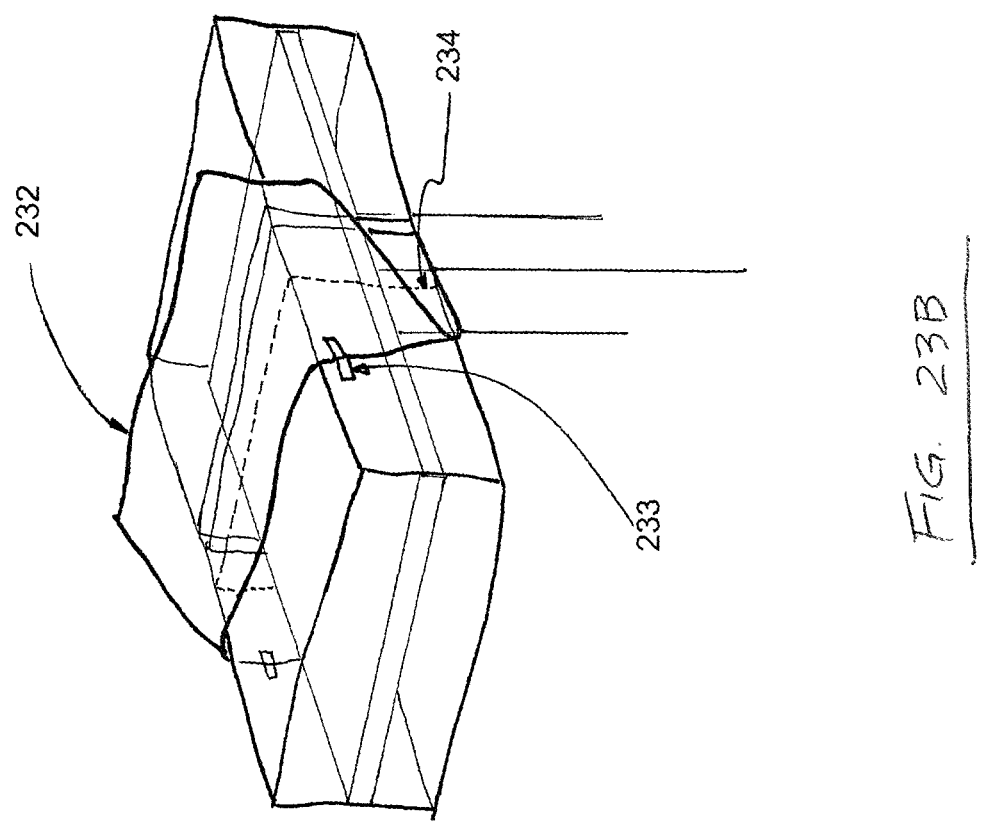
FIG. 23B is another top perspective view depicting one possible use of a draping device according to one embodiment of the present disclosure.
Figure 23C:
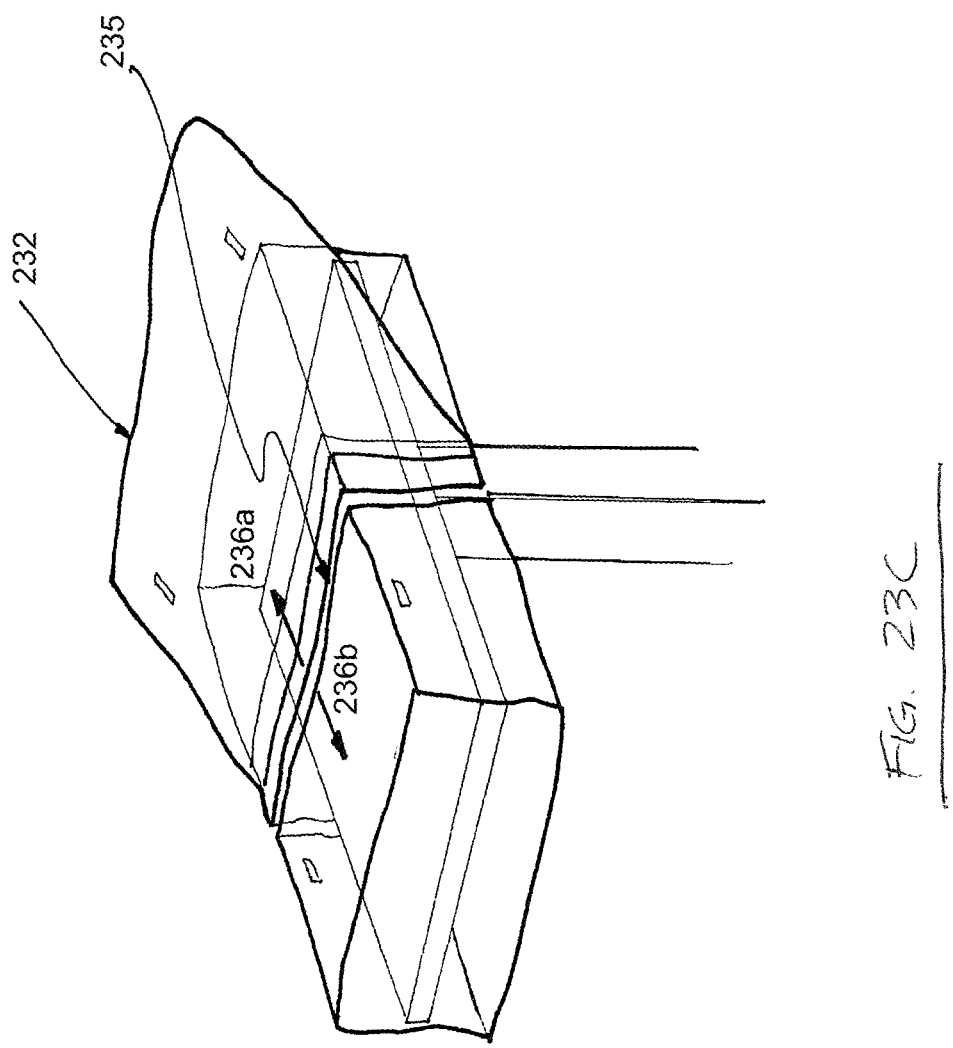
FIG. 23C is another top perspective view depicting one possible use of a draping device according to one embodiment of the present disclosure.

FIGS. 23A-C depict top perspective views of another drape 231 for maintaining the sterility of a mayo stand. As shown in FIG. 23A, the drape 231 comprises rigid or "boxed" sides and a sealed flap 232, which is held in place by at least one "tear here" label 233. The drape 231 further comprises a perforation 234, which is covered by the flap 232. As shown in FIG. 23B, the "tear here" labels 233 hold the flap 232 in place when the flap 232 is put in light tension, preventing the perforation 234 from being exposed and opening accidentally or prematurely. As shown in FIG. 23C, a greater degree of tension on the flap 232 breaks the "tear here" labels 233 and separates separable portions 235a,b along the perforation 234.

As with any radiographic and/or navigation device, the surgeon understands that these technologies serve merely as tools created to assist the surgeon in his/her task. All tools utilized in surgery have known limitations and can never be utilized with 100% reliance. According to one embodiment, an alternative design that utilizes a high light transfer lens incorporated into the plastic (or other material as clear plastic is no longer necessary if a lens is incorporated) covering the reference frame is provided to further diminution of light reflection and further enhancement of clear vision. This lens can be flat or dome shaped.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method to temporarily cover a surgical table while maintaining a sterile field during a sterile surgical procedure to lower a potential for contamination, comprising the steps of:
    draping a drape having a generally rectangular shape and an area defined by a predetermined length and a predetermined width on the surgical table, where the drape has a selectively separable portion that is initially in a closed position with a pleat covering a tear line;
    temporarily securing the drape to the surgical table;
    pulling a first end of the drape in a first direction and a second end of the drape in a second direction;
    opening the drape along the selectively separable portion from a closed position where the pleat covers the tear line, to an unclosed position;
    separating the selectively separable portion of the drape about the tear line; and
    maintaining sterility of the surgical table while the drape is moved from the closed position to the unclosed position and during the separating step by preventing an unsterile edge of the drape from contacting the sterile field.

2. The method of claim 1, further comprising the step of separating the drape about the tear line such that longitudinal effaced lateral sides of said drape separate and fall away from respective sides of the surgical table such that an unsterile edge of the drape is prevented from contacting the sterile field.

3. The method of claim 1, wherein the pleat comprises a superior cover mounted to a middle portion of the drape adjacent to the tear line, further comprising the steps of:
    pulling the superior cover in the first direction; and
    pulling the second end of the drape in the second direction.

4. A surgical drape to temporarily cover a surgical table while maintaining a sterile field during a sterile surgical procedure to lower a potential for contamination, comprising:
    a drape having a generally rectangular shape and an area defined by a predetermined length and a predetermined width, the drape having an upper portion;
    a selectively separable portion on the upper portion that extends along at least a portion of the predetermined length of the drape, said selectively separable portion having at least one pleat extending along the selectively separable portion, said selectively separable portion having at least one longitudinal perforated portion disposed below the pleat, said selectively separable portion adapted to be positioned on top of the surgical table to maintain a sterile field;
    wherein said selectively separable portion having a closed position where said pleat covers a longitudinal serrated tear line and an unclosed position where said pleat is adapted to be opened to allow said drape to be separated along said longitudinal serrated tear line, so that longitudinal effaced lateral sides of said drape separate and fall away from respective sides of the surgical table such that an unsterile edge of the drape is prevented from contacting the sterile field.

5. The surgical drape of claim 4, wherein a generally Z-shaped cross-section is formed by the selectively separable portion when in the closed position.

6. The surgical drape of claim 4, further comprising:
    a first end;
    a second end; and
    a middle portion located between the first end and the second end, and located adjacent to the longitudinal serrated tear line;
    wherein the pleat comprises a superior cover located above the upper portion and secured to the drape about the middle portion over the longitudinal serrated tear line;
    wherein the superior cover is pulled in a first direction and the second end of the drape is pulled in a second direction; and
    wherein the selectively separable portion separates about the longitudinal serrated tear line.

7. The surgical drape of claim 6, wherein the second direction is antiparallel to the first direction.

* * * * *